United States Patent
Coperet et al.

(10) Patent No.: US 10,744,494 B2
(45) Date of Patent: Aug. 18, 2020

(54) IMMOBILIZED METAL ALKYLIDENE CATALYSTS AND USE THEREOF IN OLEFIN METATHESIS

(71) Applicant: XiMo AG, Horw/Lucerne (CH)

(72) Inventors: Christophe Coperet, Zurich (CH); Margherita Puccino, Zurich (CH); Victor Mougel, Zurich (CH); Michael Buchmeiser, Stuttgart (DE); Roman Schowner, Stuttgart (DE); Csaba Hegedus, Horw/Lucerne (CH); Florian Toth, Horw/Lucerne (CH)

(73) Assignee: XiMo AG, Horw/Lucerne (CH)

( * ) Notice: Subject to any disclaimer, the term of this patent is extended or adjusted under 35 U.S.C. 154(b) by 39 days.

(21) Appl. No.: 16/062,852

(22) PCT Filed: Dec. 23, 2016

(86) PCT No.: PCT/EP2016/082600
§ 371 (c)(1),
(2) Date: Jun. 15, 2018

(87) PCT Pub. No.: WO2017/109199
PCT Pub. Date: Jun. 29, 2017

(65) Prior Publication Data
US 2019/0001315 A1   Jan. 3, 2019

(30) Foreign Application Priority Data

Dec. 23, 2015 (EP) .................................... 15003700

(51) Int. Cl.

| | |
|---|---|
| *B01J 31/22* | (2006.01) |
| *C08G 61/08* | (2006.01) |
| *C07F 7/08* | (2006.01) |
| *C07F 11/00* | (2006.01) |
| *C07C 67/333* | (2006.01) |
| *C07D 307/28* | (2006.01) |
| *C07C 1/213* | (2006.01) |
| *C07C 67/475* | (2006.01) |
| *C07C 6/04* | (2006.01) |
| *B01J 21/08* | (2006.01) |

(52) U.S. Cl.
CPC ........... *B01J 31/2278* (2013.01); *B01J 21/08* (2013.01); *B01J 31/2273* (2013.01); *B01J 31/2295* (2013.01); *C07C 1/213* (2013.01); *C07C 6/04* (2013.01); *C07C 67/333* (2013.01); *C07C 67/475* (2013.01); *C07D 307/28* (2013.01); *C07F 7/083* (2013.01); *C07F 11/00* (2013.01); *C08G 61/08* (2013.01); *B01J 2231/14* (2013.01); *B01J 2231/54* (2013.01); *B01J 2531/64* (2013.01); *B01J 2531/66* (2013.01); *C07C 2531/22* (2013.01); *C08G 2261/418* (2013.01); *Y02P 20/52* (2015.11)

(58) Field of Classification Search
CPC .............................. B01J 31/2278; C07F 11/00
See application file for complete search history.

(56) References Cited

U.S. PATENT DOCUMENTS

| | | | |
|---|---|---|---|
| 3,696,161 | A | 1/1972 | Kobetz et al. |
| 4,637,197 | A | 1/1987 | Banfield |
| 5,210,365 | A | 5/1993 | Lin |
| 5,378,783 | A | 1/1995 | Okumura et al. |
| 6,121,473 | A | 9/2000 | Schrock et al. |
| 8,993,470 | B2 | 3/2015 | Fuerstner et al. |
| 9,079,173 | B2 | 7/2015 | Schrock et al. |
| 2003/0135080 | A1 | 7/2003 | Botha et al. |
| 2005/0107529 | A1 | 5/2005 | Datta et al. |
| 2005/0124839 | A1 | 6/2005 | Gartside et al. |
| 2008/0119678 | A1 | 5/2008 | Hock et al. |
| 2011/0015430 | A1 | 1/2011 | Schrock et al. |
| 2011/0077421 | A1 | 3/2011 | Schrock et al. |
| 2011/0160472 | A1 | 6/2011 | Lemke et al. |

(Continued)

FOREIGN PATENT DOCUMENTS

| | | |
|---|---|---|
| EP | 0116408 | 1/1984 |
| EP | 0534388 | 3/1993 |

(Continued)

OTHER PUBLICATIONS

Schowner et al. "Cationic Tungsten-Oxo-Alkylidene-N-Heterocyclic Carbene Complexes: Highly Active Olefin Metathesis Catalysts" Journal of the American Chemical Society, 2015, vol. 137, pp. 6188-6191. (Year: 2015).*

(Continued)

*Primary Examiner* — Joseph R Kosack
(74) *Attorney, Agent, or Firm* — Stoel Rives LLP

(57) ABSTRACT

The invention relates to immobilized metal alkylidene catalysts. The catalysts are useful in olefin metathesis.

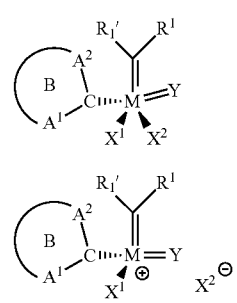

16 Claims, 5 Drawing Sheets

US 10,744,494 B2
Page 2

(56) References Cited

U.S. PATENT DOCUMENTS

| | | | |
|---|---|---|---|
| 2011/0263917 | A1 | 10/2011 | Van Hal et al. |
| 2012/0316057 | A1 | 12/2012 | Taoufik et al. |
| 2013/0006012 | A1 | 1/2013 | Firth et al. |
| 2013/0035502 | A1 | 2/2013 | Cohen et al. |
| 2013/0144102 | A1 | 6/2013 | Fuerstner et al. |
| 2013/0217906 | A1 | 8/2013 | Kunz et al. |
| 2014/0275595 | A1 | 9/2014 | Wampler et al. |
| 2014/0309466 | A1 | 10/2014 | Ondi et al. |
| 2016/0030936 | A1 | 2/2016 | Ondi et al. |
| 2016/0122375 | A1 | 5/2016 | Coperet et al. |
| 2016/0159727 | A1 | 6/2016 | Frater et al. |
| 2016/0236185 | A1* | 8/2016 | Frater .................. B01J 31/1805 |
| 2017/0348681 | A1 | 12/2017 | Coperet et al. |

FOREIGN PATENT DOCUMENTS

| | | |
|---|---|---|
| EP | 0864595 | 9/1998 |
| EP | 2703081 | 3/2014 |
| JP | 2013014562 | 5/2016 |
| WO | 2008066754 | 6/2008 |
| WO | 2009094201 | 7/2009 |
| WO | 2011007742 | 1/2011 |
| WO | 2011097642 | 8/2011 |
| WO | 2015003815 | 1/2015 |
| WO | 2015162245 | 10/2015 |

OTHER PUBLICATIONS

PCT/EP2014/000671, et al., International Search Report and Written Opinion, dated Dec. 16, 2014.
PCT/EP2014/001909, et al., International Search Report and Written Opinion, dated Aug. 7, 2014.
PCT/EP2014/001910, et al., International Search Report and Written Opinion, dated Sep. 24, 2014.
PCT/EP2014/002654, et al., International Search Report and Written Opinion, dated Dec. 17, 2014, 10 pages.
Peryshkov, et al.,Synthesis of Tungsten Oxo Alkylidene Complexes, Organometallics, 31 ,2012 ,7278-7286.
Peryshkov,Dmitry V. et al.,Z-Selective Olefin Metathesis Reactions Promoted by Tungsten Oxo Alkylidene Complexes, JACS, 133 ,Dec. 2011 ,pp. 20754-20757.
Rendon, et al.,Well-Defined Silica-Supported No-Alkylidene Catalyst Precursors Containing One or Subsitituent: Methods of Preparation and Structure-Reactivity Relationship in Alkene Metathesis, Chem. Euro. J., 15 ,2009 ,pp. 5083-5089.
Rhers, et al.,A Well-Defined, Silica-Supported Tungsten Imido Alkylidene Olefin Metathesis Catalyst, Organometallics, 25 ,2006 ,3554-3557.
Saito, et al.,1,4-Bis(trimethylsilyl)-1,4-diaza-2,5-cyclohexadienes as Strong Salt-Free Reductants for Generating Low-Valent Early Transition Metals with Electron-Donating Ligands, Journal of the American Chemical Society, 136 ,2014 ,5161-5170.
Schattenmann, et al.,Opposition—Olefin Metatheses, ,Feb. 27, 2006.
Schrock, et al.,Further Studies of Imido Alkylidene Complexes of Tungsten, Well-Characterized Olefin Metathesis Catalysts with Controllable Activity, Organometallics, 9(8) ,1990 ,2262-2275.
Schrock, et al.,High Oxidation State Multiple Metal-Carbon Bonds, Chem Rev., 102 ,2002 ,145-179.
Schrock, et al.,Multiple Metal-Carbon Bonds for Catalytic Metathesis Reactions (Nobel Lecture), Angew Chem Int Ed Engl, 45(23) ,2006 ,3748-3759.
Schrock,Richard R. et al.,Recent Advances in High Oxidation State Mo and W Imido Alkylidene Chemistry, Chemical Reviews, vol. 109 No. 8 ,Mar. 13, 2009 ,pp. 3211-3226.
Solans-Monfort, et al.,d0 Based Olefin Metathesis Catalysts, Re(=CR)(=CHR)(X)(Y): The Key Role of X and Y Ligands for Efficient Active Sites, J. Am. Chem. Soc. 2005, 127 14015-14025.
Totland, et al.,Ring Opening Metathesis Polymerization with Binaphtholate or Bibhenolate Complexes of Molybdenum, American Chemical Society, Macromolecules, 29 ,1996 ,pp. 6114-6125.
Tsai, et al.,Facile Synthesis of Trialkoxymolybdenum(VI) Alkylidyne Complexes for Alkyne Metathesis, Organometallics, 19 ,2000 ,5260-5262.
Wang, et al.,Molybdenum-Based Complexes with Two Aryloxides and a Pentafluoroimido Ligand: Catalysts for Efficient Z-Selective Synthesis of a Macrocyclic Trisubstituted alkene by Ring-Closing Metathesis, Angew Chem Int Ed Engl, 52(7) ,2013 ,1939-1943.
Yu, et al.,Enol Ethers as Substrates for Effecient Z- and Enantioselective Ring-Opening/Cross-Metathesis Reactions Promoted by Stereogenis-at-Mo Complexes: Utility in Chemical Synthesis and Mechanistice Attributes, J. Chem. Soc., 2012, 134, 2788-2799 , 2012 ,2788-2799.
Yu, et al.,Synthesis of Macrocyclic Natural Products by Catalyst-Controlled Stereoselective Ring-Closing Metathesis, Nature, vol. 479 No. 7371 ,Nov. 2, 2011 ,pp. 89-93.
Yuan,Jian et al.,Pentafluorophenylimido Alkylidene Complexes of Molybdenum and Tungsten, Organometallics, vol. 31 ,2012 ,pp. 4650-4653.
Office Action dated Dec. 11, 2018 for U.S. Appl. No. 14/904,172.
Office Action dated Dec. 17, 2018 for U.S. Appl. No. 15/536,446.
Mougel, et al.,Low Temperature Activation of Supported Metathesis Catalysts by Organosilicon Reducing Agents, ACS Central Science, 2 ,2016 ,569-576.
Notice of Allowance dated Jun. 1, 2018 for U.S. Appl. No. 14/903,119.
Notice of Allowance dated Nov. 2, 2017 for U.S. Appl. No. 14/774,404.
Office Action dated Jan. 11, 2018 for U.S. Appl. No. 14/903,119.
Office Action dated Feb. 7, 2018 for U.S. Appl. No. 15/023,892.
Office Action dated Feb. 10, 2017 for U.S. Appl. No. 14/209,313.
Office Action dated Feb. 14, 2018 for U.S. Appl. No. 14/209,313.
Office Action dated Mar. 24, 2017 for U.S. Appl. No. 14/774,404.
Office Action dated Jun. 6, 2018 for U.S. Appl. No. 15/023,892.
Office Action dated Jul. 1, 2016 for U.S. Appl. No. 14/209,313.
Office Action dated Aug. 24, 2017 for U.S. Appl. No. 14/209,313.
U.S. Appl. No. 13/639,067, et al., Notice of Allowance , dated Jan. 21, 2015 ,19 pages.
13001297.4, et al., Extended European Search Report , dated Nov. 6, 2013.
U.S. Appl. No. 14/001,811, et al., Non-Final Office Action , dated Jun. 30, 2015 ,14 pages.
U.S. Appl. No. 14/001,811, et al., Notice of Allowance , dated Oct. 9, 2015 ,5 pages.
Allen,R. D. et al.,Preparation of High Purity, Anionic Polymerization Grade Alkyl Mathacrylate Monomers, Polymer Bulletin, 15 ,1986 ,pp. 127-134.
Arndt, et al.,Synthesis and Reactions of Tunsten Alkylidene Complexes that Contain the 2,6-Dichlorophenylimido Ligand, Organometallics, 26 ,2007 ,1279-1290.
Bailey, et al.,Evaluation of Molybdenum and Tungsten Metathesis Catalysts for Homogeneous Tandem Alkane Metathesis, Organometallics, 28 ,2009 ,pp. 355-360.
Bindl, et al.,Molybdenum Nitride Complexes with Ph3SiO Ligands are Exceedingly Practical and Tolerant Precatalysts for Alkyne Metathesis and Efficient Nitrogen Transfer Agents, J Am Chem Soc., 1321 (27) ,Jul. 15, 2009 ,9468-9470.
Blanc, et al.,Direct Observation of Reaction Intermediates for a Well Defined Heterogeneous Alkene Metathesis Catalyst, PNAS, vol. 105 No. 34 ,Aug. 26, 2008 ,pp. 12123-12127.
Blanc, et al.,Dramatic Improvements of Well-Defined Silica Supported Mo-Based Olefin Metathesis Catalysts by Tuning the N-Containing Ligands, J Am Chem Soc., 129(27) ,2007 ,8434-8435.
Blanc, et al.,Highly Active, Stable, and Selective Well-Defined Silica Supported Mo Imido Olefin Metathesis Catalysts, J Am Chem Soc., 2007, 129, 1044-1045.
Blanc, et al.,Surface versus Molecular Siloxy Ligands in Well-Defined Olefin Metathesis Catalysts: [{(RO)3SiO}Mo (=NAr)(=CHtBu)(CH2tBu)], Angew. Chem. Int. Ed. 2007, 45, 1216-1220.
Chabanas, et al.,A Highly Active Well-Defined Rhenium Heterogenous Catalyst for Olefin Metathesis Prepared via Surface Organometallic Chemsitry, J. Am Chem Soc. 2001, 123, 2062-2063.

(56) References Cited

OTHER PUBLICATIONS

Dolman, Sarah J. et al., Enantioselective Synthesis of Cyclic Secondary Amines through Mo-Catalyzed Asymmetric Ring-Closing Metathesis (ARCM), Organic Letters col. 5, No. 25, 2003, pp. 4899-4902.
EP13003540.5, et al., Extended European Search Report, dated Dec. 11, 2013.
EP13003541.3, et al., European Search Report, dated Nov. 25, 2013.
Flook, Margaret M. et al., Z-Selective and Syndioselective Ring-Opening Metathesis Polymerization (ROMP) Initiated by Monoaryloxidepryrrolide (MAP) Catalysts, Macromolecules vol. 43 No. 18, 2010, pp. 7515-7522.
Fox, et al., Synthesis of Five- and Six-Coordinate Alkylidene Complexes of the Type Mo (CHR) (NAr) [OCMe (CF3) 2Sx and Their Use as Living ROMP Initiators or Wittig Reagents, American Chemical Society, Organometallics, 12, 1993, pp. 759-768.
Frater, et al., Office Action dated Jun. 9, 2017 for U.S. Appl. No. 14/903,119.
Heppekausen, et al., Practical New Silyloxy-Based Alkyne Metathesis Catalysts with Optimized Activity and Selectivity Profiles, J Am Chem Soc., vol. 132 No. 32, 2010, pp. 11045-11057.
Heppekausen, Johannes et al., Rendering Schrock-type Molybdenum Alkylidene Complexes Air Stable: User-Friendly Precatalysts for Alkene Metathesis, Angewandte Chemie (International Ed.) vol. 123, No. 34, Aug. 16, 2011, pp. 7975-7978.
Jarupatrakorn, et al., Synthesis and Characterization of Mo[OSitBu)3]4 and Mo2[OSi(OtBu)3]2 (M=Mo, W): Models for Isolated Oxo-Molybdenum and -Tungsten Sites on Silica and Precursors to Molybdena- and Tungsta-Silica Materials, Chem. Mater. 17, 2005, 1818-1828.
Jiang, et al., Highly Z-Selective Metathesis Homocoupling of Terminal Olefins, J Am Chem Soc., 131 (46), 2009, 16630-16631.
Lee, et al., Endo-Selective Enyne Ring-Closing Metathesis Promoted by Stereogenic-at-Mo Monoalkoxide and Monoaryloxide Complexes. Efficient Synthesis of Cyclic Dienes Not Accessible Through Reactions with Ru Carbines, J Am Chem Soc., 131(30), Aug. 5, 2009, 10652-10661.
Malcolmson, et al., Highly Efficient Molybdenum-Based Catalyst for Enantioselective Alkene Metathesis, Nature, 456(7224), Epub Nov. 16, 2008, Dec. 18, 2008, 933-937.
Marciniec, et al., Metathetical Activity of Allylsubstituted Silanes in the Presence of Ruthenium Catalyst, Journal of Molecular Catalysis, 90, 1994, 125-133.
Marinescu, et al., Ethenolysis Reactions Catalyzed by Imido Alkylinene Monoaryloxide Monopyrrolide (MAP) Complexes of Molybdenum, Journal of the American Chemical Society, ACS Publications, US, vol. 131 No. 31, Jul. 2009, pp. 10840-10841.
Marinescu, Smaranda C. et al., Simple Molybdenum (IV) Olefin Complexes of the Type Mo(NR)(X)(Y)(olefin), Organometallics, 29, 2010, pp. 6816-6828.
Marinescu, Smaranda C. et al., Syntheses of Variations of Stereogenic-at-Metal Imido Alkylidene Complexes of Molybdenum, Organometallics, vol. 31 No. 17, 2012, pp. 6336-6343.
Mazoyer, et al., Development of the First Well-Defined Tungsten Oxo Alkyl Derivatives Supported on Silica by SOMC: towards a Model of WO3/SiO2 Olefin Metathesis Catalyst, Chem. Commun., 46, 2010, 8944-8946.
Meek, et al., Catalytic Z-Selective Olefin Cross-Metathesis for Natural Product Synthesis, Nature 471, 2011, 461-466.
Merle, et al., On the Track to Silica-Supported Tungsten Oxo Metathesis Catalysts: Input from O Solid-State NMR, Inorg. Chem., 52, 2013, 10119-10130.
Oskam, John H. et al., Rational Isomers of Mo(VI) Alkylidene Complexes and Cis/Trans Polymer Structure: Investigations in Ring-Opening Metathesis Polymerization, J. Am. Chem. Soc. 115, 1993, pp. 11831-11845.
PCT/DE2011/000348, et al., International Search Report and Written Opinion with English Translation, dated Jul. 22, 2011, 10 pages.
PCT/DE2011/000348, et al., International Preliminary Report on Patentability, dated Oct. 9, 2012, 5 pages.
PCT/DE2012/100047, et al., International Search Report and Written Opinion (with English translation), dated Jul. 24, 2012, 10 pages.
PCT/DE2012/100047, et al., International Preliminary Report on Patentability, dated Sep. 3, 2013, 6 pages.
Office Action dated Jul. 10, 2019 for U.S. Appl. No. 15/536,446.
Office Action dated Jul. 25, 2019 for U.S. Appl. No. 14/904,172.
Lwin, et al., Olefin Metathesis by Supported Metal Oxide Catalysts, ACS Publications, 2014, 2505-2520.
Notice of Allowance dated May 15, 2019 for U.S. Appl. No. 15/023,892.
Office Action dated Apr. 2, 2019 for U.S. Appl. No. 14/904,172.
Dreisch, et al., Synthesis and Structure of Dimethoxyethane-Dichlorodioxo-Tungsten(VI)—A Highly Soluble Derivative of Tungsten Dioxidichloride, Polyhedron, 10(20-21), 1991, 2417-2421.
Duquette, et al., ECSA Studies on Silica- and Alumina-Supported Rhenium Oxide Catalysts, J Catal. 90, 1984, 362.
Gibson, et al., The Use of Silyletheres and Silythioethers in Syntheses fo Oxohalide and Thiohalide Compounds of Molybdenum and Tungsten, Polyhedron, vol. 9 No. 18, 1990, 2293-2298.
Laguerre, et al., Silylation Reductrice De Derives Monoaromatiques Fonctionnels, Journal of Organometallic Chemistry, 93, 1975, C17-C19.
Ross-Medgaarden, et al., Structural Detemination of Bulk and Surface Tungsten Oxides with UV-vis Diffuse Reflectance Spectroscopy and Raman Spectroscopy, J. Phys. Chem., 111, 2007, 15089-15099.
Schattenmann, et al., Dissertation, Anorganisches Institut der Technischen Universitat Munchen, 1997.
Office Action dated Jan. 29, 2020 for U.S. Appl. No. 14/904,172.
Office Action dated Feb. 14, 2020 for U.S. Appl. No. 15/536,446.

* cited by examiner

IMMOBILIZED METAL ALKYLIDENE CATALYSTS AND USE THEREOF IN OLEFIN METATHESIS

RELATED APPLICATIONS

This application is a National Stage Entry of International Application No. PCT/EP2016/082600, filed Dec. 23, 2016, which claims priority to European Patent Application No. 15003700.0, filed Dec. 23, 2015, each of which is incorporated herein by reference in its entirety.

FIELD OF THE INVENTION

The invention relates to immobilized metal alkylidene catalysts. The catalysts are useful in the heterogeneous catalysis of olefin metathesis.

BACKGROUND OF THE INVENTION

Due to the growing importance of olefin metathesis, a great need exists for providing suitable catalysts, which beneficially perform at industrial scale. A considerable number of organometallic alkylidene catalysts is already known to homogeneously catalyze olefin metathesis. Although it is further known that in general heterogeneous catalysts may be easier separated off from reaction mixtures than homogeneous catalysts, e.g. by filtration, which is an advantage particular at industrial scale, comparatively few heterogeneous catalysts have been accessible for olefin metathesis. Exemplarily, in the following, known heterogeneous tungsten catalysts are briefly discussed:

$WO_3$ on $SiO_2$ may be used for metathesis reactions; however, such catalysts typically operate at rather elevated temperatures. E.g., http://handle.net/10413/896 describes the performance of a $WO_3/SiO_2$ catalyst for the metathesis of 1-hexene in an isothermal, gas-phase fixed bed tubular reactor between 420 and 500° C.

Mazoyer, E. et al. report the synthesis of an alkyl oxo tungsten derivative supported on silica as olefin metathesis catalyst (Chem. Commun. 2010, 46, 8944-8946). Herein, $(tBuCH_2)_3XWO$ (X=alkyl, halogen, alkoxide, . . . ) was reported to react with silica, pretreated at 700° C., to give $(\equiv SiO)(tBuCH_2)_2Cl(W\equiv O)$ and/or $(\equiv SiO)(tBuCH_2)_3(W\equiv O)$, although a targeted alkylidene structure was $(\equiv SiO)(tBuCH_2)X(W\equiv O)(\equiv CHt-Bu)$ (X=Cl or $CH_2tBu$). However, said supported catalyst works at relatively high temperature, i.e. >100° C., and the actual nature of the active site is unknown.

Rhers et al., Organometallics, 2006, vol. 25, 3554, disclose the formation of ethene and butenes, including 1-butene, from propene in a self-metathesis reaction catalyzed by a silica supported tungsten catalyst. The catalyst has been characterized as syn-$[(\equiv SiO)(W(\equiv NAr)(\equiv CHtBu)(CH_2tBu)]$ (Ar=2,6-iPrC$_6$H$_3$) of following formula:

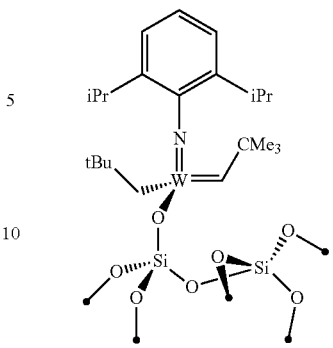

F. Blanc et al., Proc. Natl. Acad. Sci. USA, Aug. 26, 2008, vol. 105, no 34, 12123-12127, later disclose the selective formation of ethene and 2-butene from propene in a self-metathesis reaction by a silica supported tungsten catalyst. This reaction is a heterogeneously catalyzed. The catalyst is of the following structure:

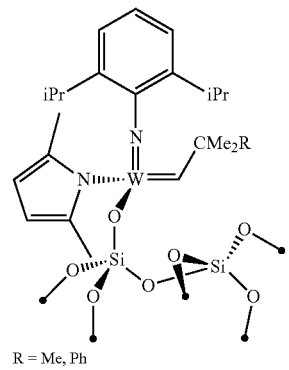

R = Me, Ph and is prepared by grafting $[W(\equiv N(2,6\text{-diisopropylphenyl})(\equiv CHtBu)(2,5\text{-Me}_2C_4H_2)_2]$ on $SiO_{2\text{-}(700)}$.

WO 2015/049047 relates to supported tungsten catalysts of the general formula

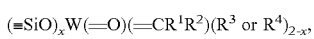

wherein each of $R^1$ and $R^2$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R; each R is independently hydrogen or an optionally substituted group selected from $C_{1\text{-}20}$ aliphatic, $C_{1\text{-}20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or: two R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or: two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur; $R^3$ and $R^4$ have independently the same meaning as $R^1$ and $R^2$; or tris($C_{1-20}$ alkyl)silyl, tris($C_{1-20}$ alkyl)silyloxy, tris($C_{1-20}$ alkoxy)silyl, tris($C_{1-20}$ alkoxy)silyloxy, tris (aryl)silyl, tris(aryl)silyloxy, tris(aryloxy)silyl, or tris(aryloxy)silyloxy; and wherein x=1 or 2.

WO 2015/162245 A2 relates to metal alkylidene N-heterocyclic carbene complexes of general Formulas (A) to (D)

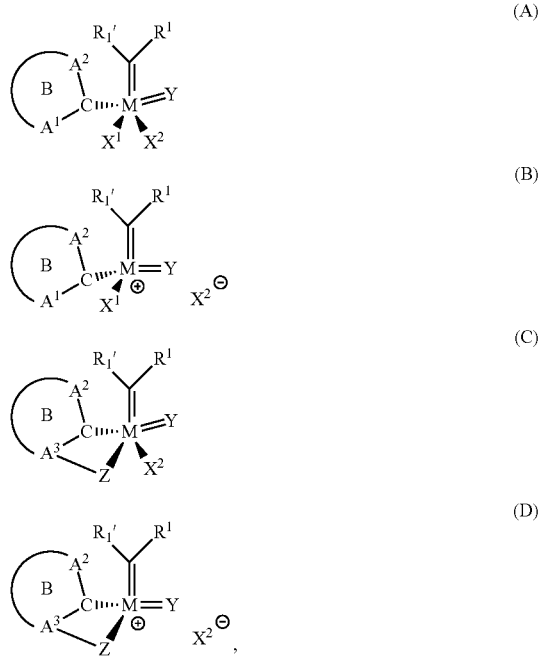

wherein $A^1$ stands for $NR^2$ or $PR^2$, $A^2$ stands for $CR^{2}R^{2'}$, $NR^2$, $PR^2$, O or S, $A^3$ stands for N or P, and C stands for a carbene carbon atom, ring B is an unsubstituted or a mono or poly-substituted 5 to 7-membered ring, substituents $R^2$ and $R^{2'}$ stand, inter alia, for a linear or branched $C_1$-$C_{10}$-alkyl group and, if $A^1$ and $A^2$ each stand for $NR^2$ or $PR^2$, are the same or different, M in Formulas (A), (B), (C) or (D) stands for Cr, Mo or W, $X^1$ or $X^2$ in Formulas (A) to (D) are the same or different and represent, inter alia, $C_1$-$C_{18}$ carboxylates and $C_1$-$C_{18}$-alkoxides, Y is inter alia oxygen or sulfur, Z is inter alia a linear or branched $C_1$-$C_{10}$-alkylenoxy group, and $R^1$ and $R^{1'}$ in Formulas (A) to (D) are, inter alia, an aliphatic or aromatic group. Ring B may be coupled via a spacer to a solid support such as glass, zirconia, titania, silica or polymer organic support materials, e.g. based on poly(methacrylates) or polystryrene/polydivinylbenzene. The compounds are suitable for use as catalysts for olefin metathesis reactions and are reported to have the advantage, compared to known Schrock carbene complexes, of displaying clearly increased tolerance to functional groups such as, in particular, aldehydes, secondary amines, nitriles, carboxylic acids and alcohols.

WO 2015/003815 discloses metathesis tungsten catalysts of the following formula

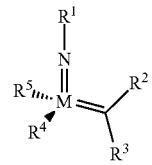

wherein M is W; $R^1$ is H, aryl, heteroaryl, alkyl, or heteroalkyl, optionally substituted, respectively; $R^2$ and $R^3$ can be the same or different and are alkyl, alkenyl, heteroalkyl, heteroalkenyl, aryl, or heteroaryl, optionally substituted, respectively, or hydrogen; $R^5$ is a residue $R^6$—X—, wherein $R^6$ is alkyl, aryl, heteroalkyl, heteroaryl, optionally substituted, respectively; ($R^7$, $R^8$, $R^9$)Si; wherein $R^7$, $R^8$, $R^9$ are independently alkyl, alkoxy, phenyl or phenoxy, optionally substituted, respectively; ($R^{10}$, $R^{11}$, $R^{12}$)C, wherein $R^{10}$, $R^{11}$, $R^{12}$ are independently phenyl, alkyl, optionally substituted, respectively; X=O, S, or $NR^{13}$, wherein $R^{13}$ is H; or alkyl or aryl, optionally substituted, respectively; or $R^5$ is $R^6$—CO—$NR^{13}$, wherein $R^6$ and $NR^{13}$ have the meaning as defined above, or wherein $R^6$ and $R^{13}$ taken together form a carbon chain having from 2 to 6 carbon atoms; $R^5$ is a 4 to 8 membered N-containing carbon ring, wherein N is linked to M; and $R^4$ is a residue O—Si(O—)$_3$, and represents silica to which M is linked forming a M—O—Si(O—)$_3$ moiety, preferably wherein silica is comprised in a solid support; under the proviso that a compound in which $R^1$=2,6-diisopropylphenyl, $R^5$ dimethylpyrrol-1-yl, $R^2$=tBu, and $R^3$=H is excluded.

OBJECTS OF THE INVENTION

In view of the few known heterogeneous catalysts suitable for olefin metathesis, and in view of the limited suitability or applicability of such catalysts with respect to the variety of metathesis reactions and olefins employed in metathesis reactions, a great need still remains for providing further heterogeneous catalysts which in particular perform at industrial scale and which may be employed at low temperatures.

Thus, one object of the present invention is the provision of immobilized catalysts which may be used for the heterogeneous catalysis of olefin metathesis, and whose efficacy may be purposively adapted to the various types of olefin metathesis, and which perform at industrial scale, preferably also at low temperatures.

SUMMARY OF THE INVENTION

The inventors of the present invention have discovered that the object is achieved with supported metal alkylidene complexes, i.e. immobilized alkylidene complexes, as defined in general Formulas I and II below in the first aspect of the invention.

Contrary to homogeneous catalysis, where the catalyst frequently has to be separated off by a rather complex processing of the reaction mixture, whereby the catalyst often is destroyed or at least considerably deteriorated in its activity, the immobilized catalysts according to the invention may be separated off from the reaction mixture via simple processing, e.g. by filtration or centrifugation, offering access to products with very low metal contamination. Furthermore, the immobilized catalysts according to the invention may be advantageously employed at rather low temperature, e.g. at 15 to 50° C. However, if necessary, the catalysts may be also employed at a rather high temperature, e.g. 150° C. or above, where they still may exhibit sufficient stability such to keep their activity.

The catalysts may be re-used in olefin metathesis. Additionally, said catalysts may be advantageously employed in continuous processes. This is particularly beneficial at an industrial scale.

As to the second aspect hereinunder, the person skilled in the art would not have expected that a compound of general Formula III or IV comprising a carbene ligand in the form of ring B can be reacted with a solid oxide to form the immobilized compound of general Formulas I or II without eliminating the carbene ring ligand B (N-heteroyclic ligand) from the compound of Formula III or IV by a nucleophilic substitution. In view of this, the formation of the immobilized compounds of Formulas I and II according to the invention still comprising said carbene ligand is surprising.

According to a first aspect, the invention relates to a compound of general Formula I or Formula II

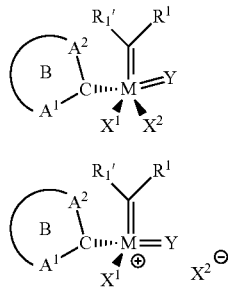

wherein:
$A^1$ is $NR^2$ or $PR^2$;
$A^2$ is $CR^2R^{2'}$, $NR^2$, $PR^2$, O or S;
C is a carbene carbon atom;
ring B includes $A^1$-C-$A^2$ and is a unsubstituted or mono- or multisubstituted 5 to 7-membered ring, which may contain besides $A^1$ and $A^2$ further heteroatoms selected from nitrogen, phosphorus, oxygen or sulfur, and the substituents of which have the meaning of $R^2$;
$R^2$ and $R^{2'}$ are independently from one another H, a linear, a partially cyclic or branched $C_1$ to $C_{18}$-alkyl residue, a linear, a partially cyclic or branched $C_1$ to $C_{18}$-alkenyl residue, a $C_3$ to $C_{12}$-cycloalkyl residue, a linear, partially cyclic or branched $C_6$ to $C_{100}$-polyoxaalkyl residue, a $C_5$ to $C_{14}$-aryl or heteroaryl residue, a $C_3$ to $C_{14}$-aryloxy residue, a linear, partially cyclic or branched $C_1$ to $C_{18}$-perfluoroalkyl residue, a linear, partially cyclic or branched $C_1$ to $C_{18}$-perchloroalkyl residue, a linear, partially cyclic or branched partially fluorinated $C_1$ to $C_{18}$-alkyl residue, a partially chlorinated linear, partially cyclic or branched $C_1$ to $C_{18}$-alkyl residue, a perfluorinated or partially fluorinated $C_6$ to $C_{14}$-aryl residue, a perchlorinated or partially chlorinated $C_6$ to $C_{14}$-aryl residue;
and, when $A^1$ and $A^2$ are $NR^2$ or $PR^2$, respectively, $R^2$ may be the same or may be different, or
$R^2$ and $R^{2'}$ taken together form a linear or branched $C_1$ to $C_{18}$-alkylene residue;
M is Cr, Mo or W;
$X^1$ is a residue of a solid oxide, wherein the solid oxide is linked to M via oxygen;
$X^2$ is selected from the group comprising or consisting of: halogenide, preferably F and Cl, $C_1$ to $C_{18}$-carboxylates, $C_1$ to $C_{18}$-alkoxides, fluorinated $C_1$ to $C_{18}$-alkoxides, $C_1$ to $C_{18}$-mono- or polyhalogenated carboxylates, unsubstituted, mono or multisubstituted $C_6$ to $C_{18}$-monophenolate, -biphenolate or -terphenolate, wherein the substituents at the monophenolate, bisphenolate or terphenolate have the meaning of halogen or $R^2$, $C_1$ to $C_{18}$-thiolate, unsubstituted, mono or multisubstituted $C_6$ to $C_{18}$-monothiophenolate, -thiobiphenolate or -thioterphenolate, wherein the substituents at the thiomonophenolate, thiobisphenolate or thioterphenolate have the meaning of halogen or $R^2$, trifluoromethane sulfonate, pyrrol-1-yl, optionally substituted with one or more of $R^2$, —NH—(CO)—$R^2$, —N($R^2$)$_2$, wherein $R^2$ is selected independently from one another, or non-coordinating anions;

Y is oxygen, sulfur, N-adamantyl, N-tert-butyl, N—($C_{6-14}$) aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;

$R^1$ and $R_1'$, are independently from one another H, linear or branched $C_1$ to $C_{18}$-alkyl or unsubstituted or substituted $C_6$ to $C_{14}$-aryl, wherein the substituents have the meaning of $R^2$.

In a preferred embodiment, is Mo or W, preferably W.

In another preferred embodiment, Y is oxygen.

In still another preferred embodiment, $R^1$ and $R_1'$ are independently from one another H and tert-butyl, or H and CMe$_2$Ph; or wherein at least one of $R^1$ and $R_1'$ is ortho-alkoxyphenyl, preferably wherein alkoxy is $C_1$ to $C_6$-alkoxy; or wherein $R^1$ and $R_1'$ are independently from one another H and ortho-alkoxyphenyl, preferably wherein alkoxy is $C_1$ to $C_6$-alkoxy.

In still another preferred embodiment, ring B is a heterocycle selected from the group comprising or consisting of: 1,3-disubstituted imidazol-2-ylidene, 1,3-disubstituted imidazolidin-2-ylidene, 1,3-disubstituted tetrahydropyrimidin-2-ylidene, 1,3-disubstituted diazepin-2-ylidene, 1,3-disubstituted dihydro-diazepin-2-ylidene, 1,3-disubstituted tetrahydrodiazepin-2-ylidene, N-substituted thiazol-2-ylidene, N-substituted thiazolin-2-ylidene, N-substituted triazol-2-ylidene, N-substituted dihydrotriazol-2-ylidene, mono- or multisubstituted triazolin-2-ylidene, N-substituted thiadiazol-2-ylidene, mono- or multisubstituted thiadiazolin-2-ylidene and mono- or multi-substituted tetrahydrotriazol-2-ylidene,
wherein the heterocycle may have one or more further substituents, wherein said substituents independently have the meaning of $R^2$ or halogen or $NR^2$.

In a further preferred embodiment, ring B is selected from 1,3-dimesitylimidazol-2-ylidene, 1,3-dimesitylimidazolidin-2-ylidene, 1,3-di-tert-butylimidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene.

In one embodiment, when $X^2$ is a non-coordinating anion, said anion in Formula II is selected e.g. from tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

In a further preferred embodiment, the solid oxide is selected from the group comprising or consisting of: silica, titania, zirconia, cerium oxide, alumina, or a mixture of two or more thereof.

In a further preferred embodiment, the solid oxide is silica and $X^1$ is O—Si(O—)$_3$.

In a further preferred embodiment, silica is comprised in a solid support.

In one embodiment,
M is selected from Mo or W;
Y is selected from oxygen, sulfur, N-adamantyl, N-tert-butyl, N—(C$_{6-14}$)aryl, wherein aryl may be substituted with one or more of halogen, linear or branched C$_1$ to C$_{18}$-alkyl, linear or branched C$_1$ to C$_{18}$-alkyloxy or substituted or unsubstituted phenyl, the substituents of which have the meaning of $R^2$;
ring B is selected from 1,3-dimesitylimidazol-2-ylidene, 1,3-dimesitylimidazolidin-2-ylidene, 1,3-di-tert-butylimidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene;
$R^1$ and $R_1{'}$ are independently from one another H and tert-butyl, or H and CMe$_2$Ph; or wherein at least one of $R^1$ and $R_1{'}$ is ortho-alkoxyphenyl, preferably wherein alkoxy is C$_1$ to C$_6$-alkoxy; or wherein $R^1$ and $R_1{'}$ are independently from one another H and ortho-alkoxyphenyl, preferably wherein alkoxy is C$_1$ to C$_6$-alkoxy;
$X^1$ is (—O—)$_3$Si—O—; and
$X^2$ is selected from the group comprising or consisting of halide, preferably F and Cl, C$_1$ to C$_{18}$-alkoxides, fluorinated C$_1$ to C$_{18}$-alkoxides, trifluoromethane sulfonate, tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

In one embodiment,
M is selected from Mo or W;
Y is selected from oxygen, N-adamantyl, N-tert-butyl, N—(C$_{6-14}$)aryl, wherein aryl may be substituted with one or more of halogen, linear or branched C$_1$ to C$_{18}$-alkyl, linear or branched C$_1$ to C$_{18}$-alkyloxy or substituted or unsubstituted phenyl, the substituents of which have the meaning of $R^2$;
ring B is selected from 1,3-dimesitylimidazol-2-ylidene, 1,3-dimesitylimidazolidin-2-ylidene, 1,3-di-tert-butylimidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene;
$R^1$ and $R_1{''}$ are independently from one another H and tert-butyl, or H and CMe$_2$Ph; or wherein at least one of $R^1$ and $R_1{'}$ is ortho-alkoxyphenyl, preferably wherein alkoxy is C$_1$ to C$_6$-alkoxy; or wherein $R^1$ and $R_1{'}$ are independently from one another H and ortho-alkoxyphenyl, preferably wherein alkoxy is C$_1$ to C$_6$-alkoxy;
$X^1$ is (—O—)$_3$Si—O—; and
$X^2$ is selected from the group comprising or consisting of F and Cl, fluorinated C$_1$ to C$_{18}$-alkoxides, trifluoromethane sulfonate, tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

In one embodiment,
M is selected from Mo or W;
Y is selected from oxygen, N-adamantyl, N-tert-butyl, N—(C$_{6-14}$)aryl, wherein aryl may be substituted with one or more of halogen, linear or branched C$_1$ to C$_{18}$-alkyl, linear or branched C$_1$ to C$_{18}$-alkyloxy or substituted or unsubstituted phenyl, the substituents of which have the meaning of $R^2$;
ring B is selected from 1,3-dimesitylimidazol-2-ylidene, 1,3-dimesitylimidazolidin-2-ylidene, 1,3-di-tert-butylimidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene;
$R^1$ and $R_1{'}$ are independently from one another H and tert-butyl, or H and CMe$_2$Ph; or wherein at least one of $R^1$ and $R_1{'}$ is ortho-alkoxyphenyl, preferably wherein alkoxy is C$_1$ to C$_6$-alkoxy; or wherein $R^1$ and $R_1{'}$ are independently from one another H and ortho-alkoxyphenyl, preferably wherein alkoxy is C$_1$ to C$_6$-alkoxy;
$X^1$ is (—O—)$_3$Si—O—; and
$X^2$ is selected from the group comprising or consisting of F and Cl, trifluoromethane sulfonate, tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

In one embodiment,
M is W;
Y is oxygen;
ring B is 1,3-dimesitylimidazol-2-ylidene;
$R^1$ and $R_1{'}$ are independently from one another H and CMe$_2$Ph;
$X^1$ is (—O—)$_3$Si—O—; and
$X^2$ is trifluoromethanesulfonate;
or
M is W;
Y is oxygen;
ring B is 1,3-dimesitylimidazol-2-ylidene;
$R^1$ and $R_1{''}$ are independently from one another H and CMe$_2$Ph;
$X^1$ is (—O—)$_3$Si—O—; and
$X^2$ is tetrakis(3,5-bis(trifluoromethyl)phenyl)borate;
or
M is W;
Y is N-tert-butyl;
ring B is 4,5-dichloro-1,3-dimethyl-imidazol-2-ylidene;
$R^1$ and $R_1{'}$ are independently from one another H and tert-butyl;
$X^1$ is (—O—)$_3$Si—O—; and
$X^2$ is Cl;

or
M is W;
Y is N-tert-butyl;
ring B is 4,5-dichloro-1,3-dimethyl-imidazol-2-ylidene;
$R^1$ and $R_1'$ are independently from one another H and tert-butyl;
$X^1$ is $(-O-)_3Si-O-$; and
$X^2$ is tetrakis(nonafluoro-t-butoxy)aluminate;
or
M is W;
Y is O;
ring B is 1,3,5-triphenyl-triazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is N-2,6-dichlorophenyl;
ring B is 1,3,5-triphenyl-triazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is N-2-trifluoromethylphenyl;
ring B is 1,3,5-triphenyl-triazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is N-3,5-dimethylphenyl;
ring B is 1,3,5-triphenyl-triazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate; or
M is Mo;
Y is N-2,6-dimethylphenyl;
ring B is 1,3-dimesitylimidazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is N-2,6-dimethylphenyl;
ring B is 1,3-dimesitylimidazolidin-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is O;
ring B is 1,3-dimesitylimidazol-2-ylidene;
$R^1$ and $R_1'$ are independently from one another H and 2-methoxyphenyl;
$X^1$ is $(-O-)_3Si-O-$; and
$X^2$ is tetrakis(3,5-bis(trifluoromethyl)phenyl)borate;
or
M is Mo;
Y is N-2,6-dimethylphenyl;
ring B is 1,3-dimesitylimidazolidin-2-ylidene;

$R^1$ and $R_1'$ are independently from one another H and 2-methoxyphenyl;
$X^1$ is $(-O-)_3Si-O-$; and
$X^2$ is tetrakis(3,5-bis(trifluoromethyl)phenyl)borate;
or
M is Mo;
Y is N-2,6-dimethylphenyl;
ring B is 1,3-dimesitylimidazol-2-ylidene;
$R^1$ and $R_1'$ are independently from one another H and 2-methoxyphenyl;
$X^1$ is $(-O-)_3Si-O-$; and
$X^2$ is tetrakis(3,5-bis(trifluoromethyl)phenyl)borate;
or
M is Mo;
Y is N-2-tert-butlylphenyl;
ring B is 1,3-dimesitylimidazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is W;
Y is O;
ring B is 1,3-dimesitylimidazol-2-ylidene;
$R^1$ and $R_1'$ are independently from one another H and $CMe_2Ph$;
$X^1$ is $(-O-)_3Si-O-$; and
$X^2$ is tetrakis(pentafluorophenyl)borate.

According to a second aspect, the invention relates to a method of making a compound of the general Formula I or II as defined in the first aspect, or any embodiment defined therein, comprising at least the following step (S):

(S) reacting a solid oxide with a compound of the general Formula III or IV

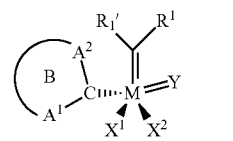

III

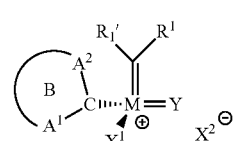

IV wherein $A^1$, $A^2$, C, ring B, $X^2$, $R^1$ and $R^{1'}$ have the meaning as defined in the first aspect with respect to compounds of general Formula I and II; and $X^1$ is $C_{0-8}$ sulfonate, preferably $FSO_2O$, $CF_3SO_2O$, $C_4F_9SO_2O$, $CH_3SO_2O$, p-$CH_3C_6H_4SO_2O$; halogenide, preferably chloride, bromide and iodide; nitrate and phosphate and $C_{1-8}$ esters of phosphate; $C_{1-8}$ alcoholate and fluorinated $C_{1-8}$ alcoholate, preferably $(CF_3)(CH_3)CH-O$, $(CF_3)_2CH-O$ or $(CF_3)_3C-O$, or $C_6F_5-O$.

In a preferred embodiment, the method further comprises step (R) prior to step (S):

(R): heating the solid oxide in vacuo.

In a further embodiment, a passivation step of e.g. trimethyl silylation, may be conducted before or after the grafting of the catalyst onto the solid oxide.

In a preferred embodiment, the solid oxide is silica.

In a preferred embodiment, silica is comprised in a solid support.

According to a third aspect, the invention relates to a method of forming an olefin from a first and a second olefin in a metathesis reaction, comprising step (T):

(T): reacting the first olefin with the second olefin in the presence of a compound of general Formula I or II as defined in the first aspect, or made according to a method as defined in the second aspect.

wherein the first and the second olefin may be the same or may be different from one another.

According to a fourth aspect, the invention relates to a method of converting a compound of general Formula I or general Formula II as defined in the first aspect into a compound of general Formula VI or general Formula VII, the method comprising at least step (U):

(U): reacting said compound of general Formula I with a compound of general Formula V to yield said compound of general Formula VI, or reacting said compound of general Formula II with a compound of general Formula V to yield said compound of general Formula VII, $$CH_2=CR_1'R^1 \quad \text{V}$$

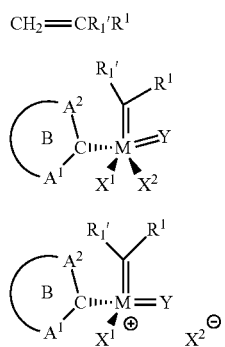

wherein at least one of $R_1'$ and $R^1$ in compound of Formula V is different from at least one of $R_1'$ and $R^1$ as defined in general Formula I or general Formula II, and wherein $R_1'$ and $R^1$ in general Formula VI and general Formula VII have the same meaning as in general Formula V.

BRIEF DISCUSSION OF THE FIGURES

Figure 3:
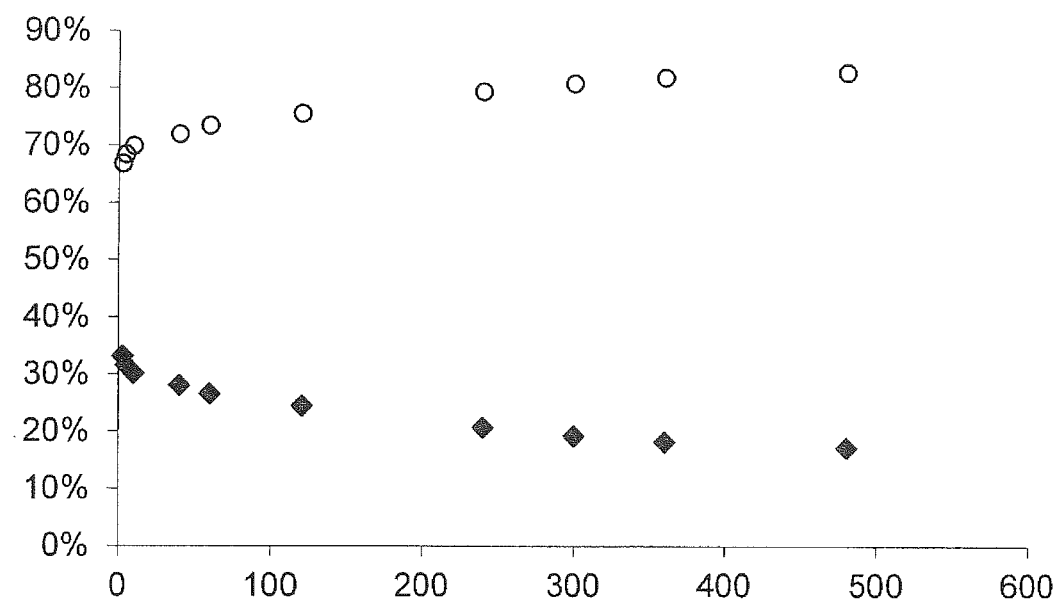

FIG. 3 shows the E/Z selectivity in % (y-axis) versus time in minutes (x-axis) for the self-metathesis of cis-4-nonene by compound 1@SiO$_2$ according to the invention (0.1 mol %). E (white circles); Z (black diamonds).

Figure 4:
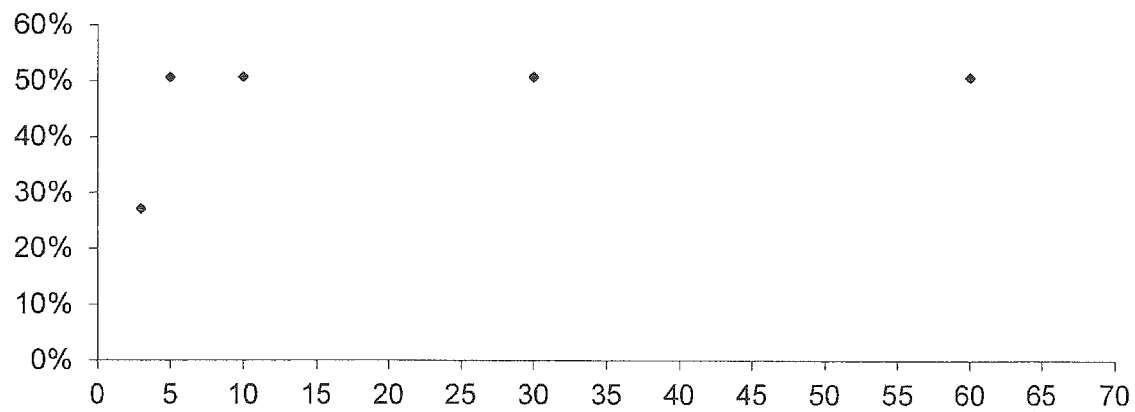

FIG. 4 shows the conversion of cis-4-nonene in the metathesis thereof using compound 2@SiO2 according to the invention (0.1 mol %, 30° C.). The x-axis denotes the time in minutes and the y-axis the conversion in %.

Figure 5:
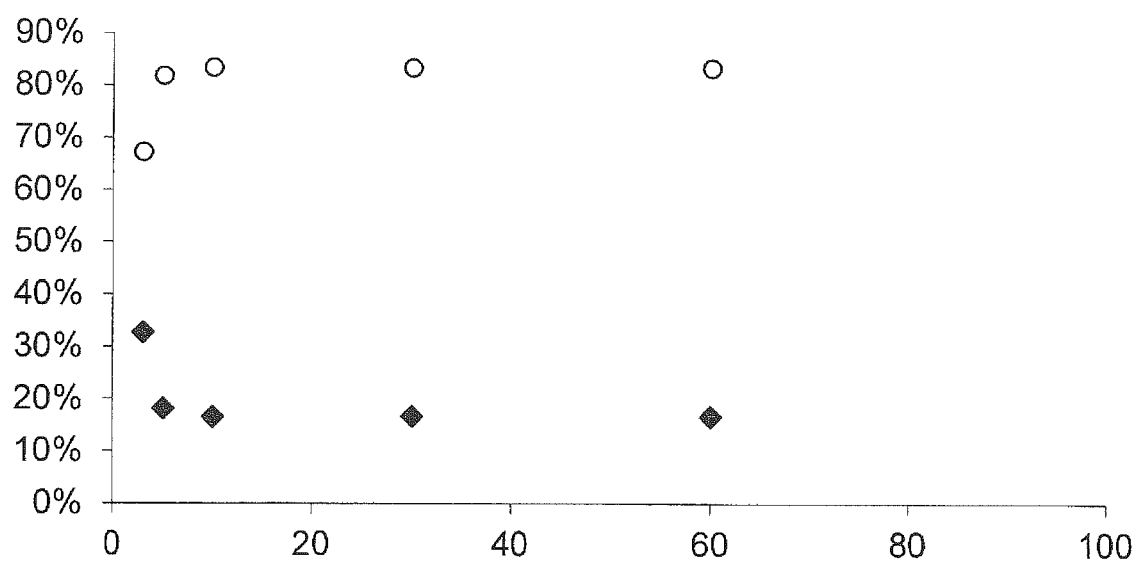

FIG. 5 shows the E/Z selectivity in % (y-axis) versus time in minutes (x-axis) for the self-metathesis of cis-4-nonene by compound 2@SiO$_2$ according to the invention (0.1 mol %). E (white circles); Z (black diamonds).

Figure 6:
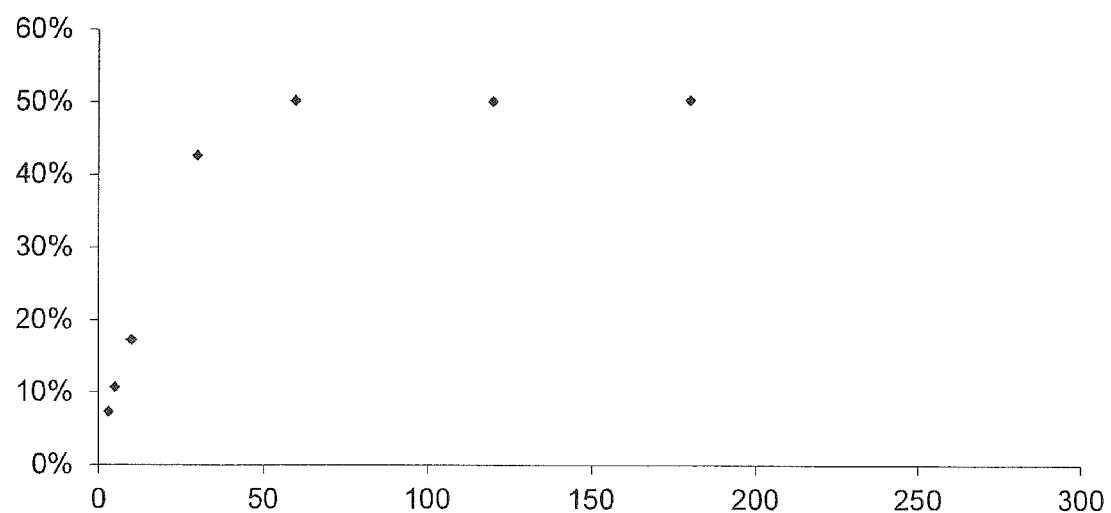

FIG. 6 shows the conversion of non-4-ene in the metathesis thereof using compound 2@SiO2 according to the invention (0.02 mol %, 30° C.). The x-axis denotes the time in minutes and the y-axis the conversion in %.

Figure 7:
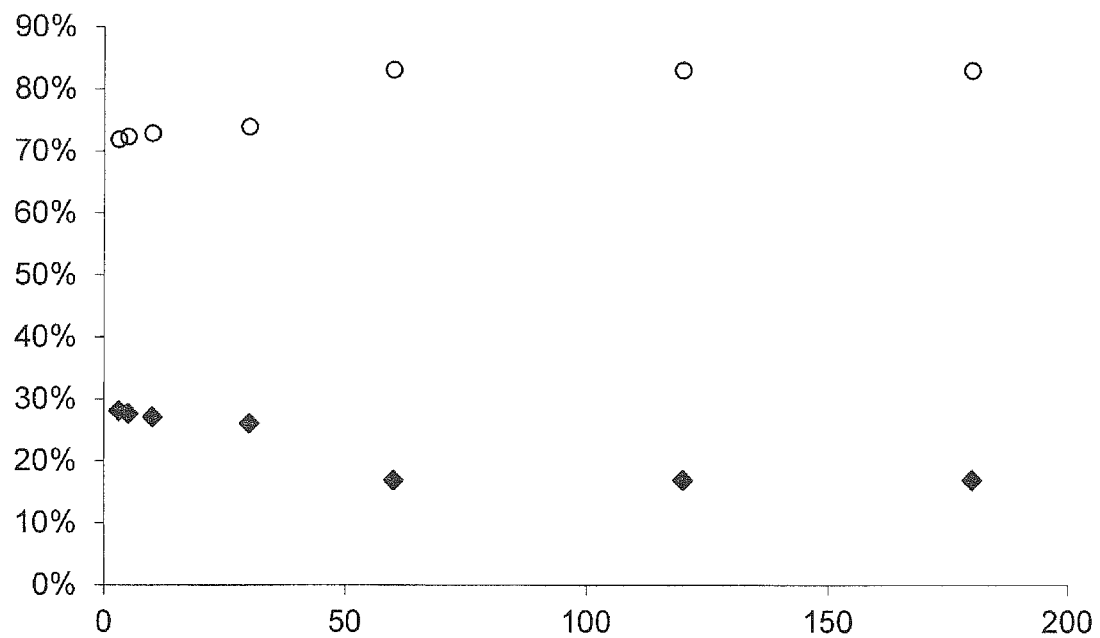

FIG. 7 shows the E/Z selectivity in % (y-axis) versus time in minutes (x-axis) for the self-metathesis of cis-4-nonene by compound 2@SiO$_2$ according to the invention (0.02 mol %). E (white circles); Z (black diamonds).

Figure 8:
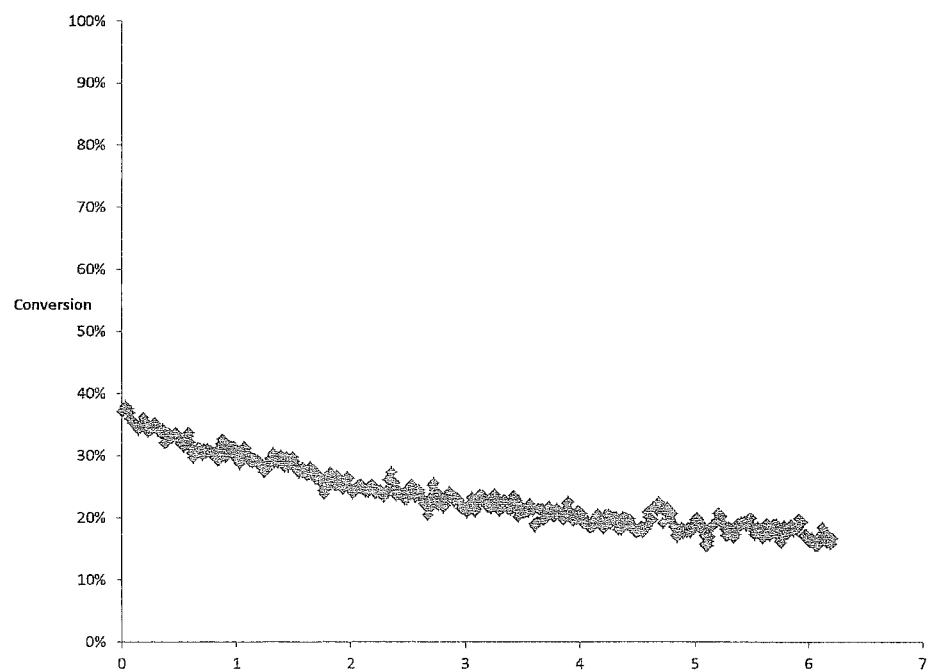

FIG. 8 shows the conversion of propene by compound 2@SiO$_2$ according to the invention under flow conditions in a flow reactor (x-axis: time in days; Y-axis conversion in %).

Figure 9:
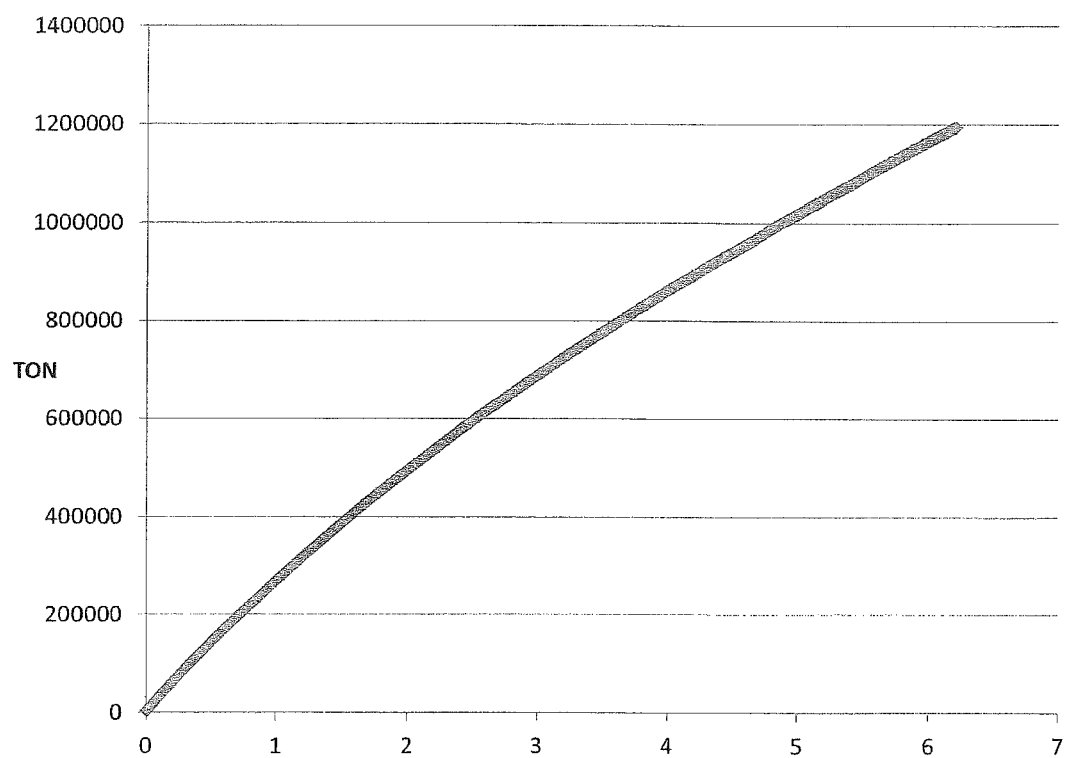

FIG. 9 shows TONs (y-axis) of propene metathesis by compound 2@SiO$_2$ under flow conditions (x-axis: time in days).

DETAILED DESCRIPTION OF THE INVENTION

Definitions as Used in this Disclosure

In the following, all terms and symbols in quotation marks are used in the meaning of the invention The term "comprising" is used in the meaning of "including but not limited to".

The term "consisting of" is used in the meaning "including and limited to".

The term "$C_{1-20}$ aliphatic" encompasses both alkyl and alkenyl.

The term "alkyl" encompasses saturated aliphatic groups, including straight-chain alkyl groups, branched-chain alkyl groups, cycloalkyl (alicyclic) groups, alkyl substituted cycloalkyl groups, and cycloalkyl substituted alkyl groups and alkyl groups substituted with aryl. In certain embodiments, a straight chain or branched chain alkyl has about 20 or fewer carbon atoms in its backbone (e.g., $C_{1-20}$ for straight chain, $C_{3-20}$ for branched chain). Likewise, cycloalkyls have from about 3 to about 10 carbon atoms in their ring structure, and alternatively about 5, 6 or 7 carbons in the ring structure. In some embodiments, an alkyl group may be a lower alkyl group, wherein a lower alkyl group comprises 10 or fewer carbon atoms in its backbone (e.g., $C_{1-10}$ for straight chain lower alkyls).

In one embodiment, the term "alkyl" encompasses $C_{1-4}$ alkyl such as methyl, isopropyl ("iPr") or t-butyl ("tBu"). The term "tBuF3" denotes a tertiary butyl group $(CF_3)(CH_3)_2C$. The term "tBuF6" denotes a tertiary butyl group $(CF_3)_2(CH_3)C$. The term "tBuF9" denotes a tertiary butyl group $(CF_3)_3C$.

The term "alkyl" further encompasses bridged hydrocarbon residues such as the adamantyl residue, particularly the adamant-1-yl residue.

The term "alkyl" further encompasses annelated ring systems such as the fluorene-9-yl residue such as the 9-phenyl-fluorene-9-yl residue.

The term "alkenyl" refers to olefinic groups as described below. The alkenyl group may be optionally substituted with the substituents defined above.

The term "$C_{1-20}$ heteroalkyl" refers to alkyl groups in which one or more atoms is a heteroatom (e.g., oxygen, nitrogen, sulfur, and the like). Examples of heteroalkyl groups include, but are not limited to, alkoxy, poly(ethylene glycol)-,alkyl-substituted amino, tetrahydrofuranyl, piperidinyl, morpholinyl, etc.

The term "alkoxy" refers to the group —O-alkyl, wherein alkyl has the meaning as defined above in connection with the term "alkyl".

The term "aryl ring" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated π electron system, while other, adjoining rings can be cycloalkyls, cycloalkenyls, cycloalkynyls, aryls, and/or heterocyclyls. The aryl group may be optionally substituted.

The term "aryloxy" refers to the group —O-aryl, wherein aryl has the meaning as defined above in connection with the term "aryl ring".

The term "$C_{1-8}$ esters of phosphate" denotes an ester of phosphoric acid in which the alcohol moiety comprises from 1 to 8 carbon atoms.

The term "$C_{1-8}$ alcoholate" denotes an alcoholate comprising from 1 to 8 carbon atoms.

The term "carbocyclic aryl groups" refers to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the aryl groups may include monocyclic carbocyclic aryl groups and polycyclic or fused compounds (e.g., two or more adjacent ring atoms are common to two adjoining rings) such as naphthyl group. Non-limiting examples of aryl groups include phenyl, naphthyl, tetrahydronaphthyl, indanyl, indenyl, and the like.

The term "heteroaryl" refers to aryl groups in which one or more atoms is a heteroatom (e.g., oxygen, nitrogen, sulfur, and the like), optionally substituted. Examples of aryl and heteroaryl groups include, but are not limited to, phenyl, pyrrolyl, furanyl, imidazolyl, oxazolyl, thiazolyl, triazolyl, pyrazolyl, pyridinyl, pyrazinyl, pyridazinyl and pyrimidinyl, and the like.

The terms "substituted" and "optionally substituted" are contemplated to include all permissible substituents of organic compounds, "Permissible" being in the context of the chemical rules of valence known to those of ordinary skill in the art. Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl.

The term "solid support" encompasses any material that includes a solid oxide such as silica as such or silica in combination with other materials. Accordingly, silica may be used in the form of a mixed oxide, e.g. a mixed oxide of silica and alumina or silica and zirconia or oxides such as $TiO_2$, $V_2O_5$, $MoO_2$, $WO_3$, silicates, zeolites, or sulfates or phosphates of alkali metals or earth alkali metals.

Preferably, in the present invention, silica is used as solid support.

The term "silica" encompasses compounds of Formula $SiO_2$ and further encompasses porous or non-porous silica.

The term "silica" encompasses compounds of Formula $SiO_2$ which comprise organosilyl groups such as trimethylsilyl groups.

The term "silica" further encompasses partially dehydroxylated and/or dehydrated silica. Dehydroxylation and/or dehydration may be performed using elevated temperature or elevated temperature and vacuum. Residual hydroxyl content may be determined by titration with MeMgCl.

The term "$SiO_{2-(700)}$" denotes partially dehydroxylated and dehydrated silica at 700° C.

The term "metathesis" refers to alkene (olefin) metathesis, and to the various types of metathesis such as cross metathesis, ring opening metathesis, ring opening polymerization metathesis, ring closing metathesis, ethenolysis, self or homo metathesis.

The term "cross metathesis" encompasses the reaction between two different olefins.

The term "ring opening metathesis" encompasses the ring opening of a cyclic alkene.

The term "ring opening polymerization metathesis" encompasses the ring opening of a cyclic alkene, wherein the ring-opened product polymerizes in a chain-growth polymerization to form a polymer containing olefinic bonds.

The term "ring closing metathesis" encompasses the ring closing of a diene.

The term "ethenolysis" encompasses the reaction of an olefin having an internal olefinic bond with ethylene.

The term "self or homo metathesis (SM)" encompasses the reaction between two identical olefins. The term is synonymously used with the term "homo cross metathesis (HCM)" and also encompasses the formation of an internal olefin from two identical olefins.

The term "reacting" encompasses a reaction in which in a compound a new bond is formed.

The term "olefinic double bond" refers to a carbon-carbon double bond or ethylenic double bond in a first olefin and a second olefin.

The term "first or second olefin" is in one embodiment synonymously used with the term "first and second olefin".

The term "olefin" as used in the terms "first olefin" and "second olefin" refers to any species having at least one ethylenic double bond such as linear and branched chain aliphatic olefins, cycloaliphatic olefins, or aryl substituted olefins. Olefins may comprise terminal double bond(s) ("terminal olefin") and/or internal double bond(s) ("internal olefin") and can be cyclic or acyclic, linear or branched, optionally substituted. The total number of carbon atoms can be from 2 to 100, or from 2 to 40; the double bonds of a terminal olefin may be mono- or bi-substituted and the double bond of an internal olefin may be bi-, tri-, or tetrasubstituted. In some cases, an internal olefin is bisubstituted.

Non-limiting examples of terminal olefins are substituted and unsubstituted linear alkyl internal olefins such as $C_4$-$C_{30}$ olefins (e.g., 1-butene, 1-pentene, 1-hexene, 1-heptene, 1-octene, 1-decene, 1-dodecene, 1-tetradecene, 1-hexadecene, 1-octadecene, 1-eicosene, allylbenzene, allyltrimethylsilane, methyl-10-undecenoate, allylboronic acid pinacol ester, allylbenzylether, N-allyl-4-methylbenzenesulfonamide, allylaniline, methyl-9-decenoate, allyloxy(tert-butyl) dimethyl silane, allylcyclohexane, etc.).

In one embodiment, the olefin having a terminal olefinic double bond is of Formula $RCH=CH_2$, wherein R is selected from H, alkyl, alkenyl, aryl, heteroalkyl, heteroalkenyl, heteroaryl, or acyl, optionally substituted.

The term "cyclic olefin" refers to any cyclic species comprising at least one ethylenic double bond in a ring. The atoms of the ring may be optionally substituted. The ring may comprise any number of carbon atoms and/or heteroatoms. In some cases, the cyclic olefin may comprise more than one ring. A ring may comprise at least 3, at least 4, at least 5, at least 6, at least 7, at least 8, or more, atoms. Non-limiting examples of cyclic olefins include norbornene, dicyclopentadiene, bicyclo compounds, oxabicyclo compounds, and the like, all optionally substituted. "Bicyclo compounds" are a class of compounds consisting of two rings only, having two or more atoms in common. "Oxabicyclo compounds" are a class of compounds consisting of two rings only, having two or more atoms in common, wherein at least one ring comprises an oxygen atom.

In one embodiment, the first and the second olefin or the first and the second olefin may bear one or more functional groups.

Preferably, the first and the second olefin or the first or the second olefin may bear one or more functional groups independently selected from the group consisting of ether, ester, amide, amine, halogen, nitrile, thioether, thioester, aryl, or heteroaryl.

In a further preferred embodiment, the first and the second olefin or the first or the second olefin bear one or more functional groups independently selected from alkoxy, aryloxy, perhaloalkoxy, arylalkoxy, heteroaryl, heteroaryloxy, heteroarylalkyl, heteroarylalkoxy, amino, halogen, alkylthio, oxo, carboxy esters, carboxamido, acyloxy, aminoalkyl, alkylaminoaryl, alkylaminoalkyl, alkoxyaryl, arylamino, arylalkylamino, alkylsulfonyl, carboxamidoalkylaryl, carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl.

First Aspect: Compounds According to the Invention

According to a first aspect, the invention relates to a compound of general Formula I or Formula II

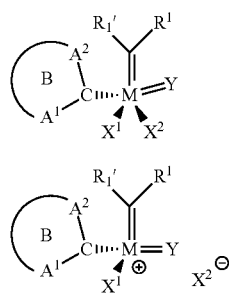

In its broadest meaning, the term or symbol "M" denotes any metal being capable of forming a compound of Formula I or Formula II.

Specifically, M denotes a metal of group VI B of the Periodic Table.

More specifically, M denotes Cr, Mo or W.

Still more specifically, denotes Mo or W.

In a preferred embodiment, M is W.

In its broadest meaning, the term or symbol "ring B" denotes any ring system being capable of forming a carbene which in turn is capable of forming a bond between the carbene carbon atom of the ring and M.

In one embodiment, the term or symbol "ring B" denotes a heterocycle being capable of forming a carbene.

More specifically, the term or symbol "ring B" is an unsubstituted, a mono- or a multisubstituted 5 to 7-membered ring.

Still more specifically, the term or symbol "ring B" includes $A^1$-C-$A^2$ and is unsubstituted or mono- or multisubstituted 5 to 7-membered ring, which may contain besides $A^1$ and $A^2$ further heteroatoms selected from nitrogen, phosphorus, oxygen or sulfur, and the substituents of which have the meaning of $R^2$.

$R^2$ is H, a linear, a partially cyclic or branched $C_1$ to $C_{18}$-alkyl residue, a linear, a partially cyclic or branched $C_1$ to $C_{18}$-alkenyl residue, a $C_3$ to $C_{12}$-cycloalkyl residue, a linear, partially cyclic or branched $C_6$ to $C_{100}$-polyoxaalkyl residue, a $C_5$ to $C_{14}$-aryl or heteroaryl residue, a $C_3$ to $C_{14}$-aryloxy residue, a linear, partially cyclic or branched $C_1$ to $C_{18}$-perfluoroalkyl residue, a linear, partially cyclic or branched $C_1$ to $C_{18}$-perchloroalkyl residue, a linear, partially cyclic or branched partially fluorinated $C_1$ to $C_{18}$-alkyl residue, a partially chlorinated linear, partially cyclic or branched $C_1$ to $C_{18}$-alkyl residue, a perfluorinated or partially fluorinated $C_6$ to $C_{14}$-aryl residue, a perchlorinated or partially chlorinated $C_6$ to $C_{14}$-aryl residue.

In one embodiment, $A^1$ is $NR^2$ or $PR^2$.

In one embodiment, $A^2$ is $CR^2R^{2'}$, $NR^2$, $PR^2$, O or S.

$R^{2'}$ is H, a linear, a partially cyclic or branched $C_1$ to $C_{18}$-alkyl residue, a linear, a partially cyclic or branched $C_1$ to $C_{18}$-alkenyl residue, a $C_3$ to $C_{12}$-cycloalkyl residue, a linear, partially cyclic or branched $C_6$ to $C_{100}$-polyoxaalkyl residue, a $C_5$ to $C_{14}$-aryl or heteroaryl residue, a $C_3$ to $C_{14}$-aryloxy residue, a linear, partially cyclic or branched $C_1$ to $C_{18}$-perfluoroalkyl residue, a linear, partially cyclic or branched $C_1$ to $C_{18}$-perchloroalkyl residue, a linear, partially cyclic or branched partially fluorinated $C_1$ to $C_{18}$-alkyl residue, a partially chlorinated linear, partially cyclic or branched $C_1$ to $C_{18}$-alkyl residue, a perfluorinated or partially fluorinated $C_6$ to $C_{14}$-aryl residue, a perchlorinated or partially chlorinated $C_6$ to $C_{14}$-aryl residue.

In one embodiment, when $A^1$ and $A^2$ are $NR^2$ or $PR^2$, respectively, $R^2$ may be the same or may be different, or $R^2$ and $R^{2'}$ taken together form a linear or branched $C_1$ to $C_{18}$-alkylene residue.

In one embodiment, $R^2$ and $R^{2'}$ are independently from one another H, a linear, a partially cyclic or branched $C_1$ to $C_{18}$-alkyl residue, a linear, a partially cyclic or branched $C_1$ to $C_{18}$-alkenyl residue, a $C_3$ to $C_{12}$-cycloalkyl residue, a linear, partially cyclic or branched $C_6$ to $C_{100}$-polyoxaalkyl residue, a $C_5$ to $C_{14}$-aryl or heteroaryl residue, a $C_3$ to $C_{14}$-aryloxy residue, a linear, partially cyclic or branched $C_1$ to $C_{18}$-perfluoroalkyl residue, a linear, partially cyclic or branched $C_1$ to $C_{18}$-perchloroalkyl residue, a linear, partially cyclic or branched partially fluorinated $C_1$ to $C_{18}$-alkyl residue, a partially chlorinated linear, partially cyclic or branched $C_1$ to $C_{18}$-alkyl residue, a perfluorinated or partially fluorinated $C_6$ to $C_{14}$-aryl residue, a perchlorinated or partially chlorinated $C_6$ to $C_{14}$-aryl residue; and, when $A^1$ and $A^2$ are $NR^2$ or $PR^2$, respectively, $R^2$ may be the same or may be different, or $R^2$ and $R^{2'}$ taken together form a linear or branched $C_1$ to $C_{18}$-alkylene residue.

C is a carbene carbon atom.

In its broadest meaning, $X^1$ in a compound of Formula I or Formula II is a residue of a solid oxide, wherein the solid oxide is linked to M via oxygen.

The term "$X^1$ is a residue of a solid oxide, wherein the solid oxide is linked to M via oxygen" means that $X^1$ is a residue of a solid oxide, wherein the solid oxide is linked to M via oxygen, wherein said oxygen is part of said solid oxide. E.g., if the solid oxide is silica, titania, zirconia, cerium oxide, or alumina, said oxygen being linked to M is in turn linked to Si, Ti, Zr, Ce, or Al.

Further exemplary, if the solid oxide is silica, this term is synonymously used with the term "wherein the solid oxide is silica and $X^1$ is O—Si(O—)$_3$". Thus, the solid oxide is directly linked to M.

In its broadest meaning, $X^2$ is selected from the group comprising or consisting of halogenide, preferably F and Cl, $C_1$ to $C_{18}$-carboxylates, $C_1$ to $C_{18}$-alkoxides, fluorinated $C_1$ to $C_{18}$-alkoxides, $C_1$ to $C_{18}$-mono- or polyhalogenated carboxylates, unsubstituted, mono or multisubstituted $C_6$ to $C_{18}$-monophenolate, -biphenolate or -terphenolate, wherein the substituents at the monophenolate, bisphenolate or terphenolate have the meaning of halogen or $R^2$, $C_1$ to $C_{18}$-thiolate, unsubstituted, mono or multisubstituted $C_6$ to $C_{18}$-monothiophenolate, -thiobiphenolate or -thioterphenolate, wherein the substituents at the thiomonophenolate, thiobisphenolate or thioterphenolate have the meaning of halogen or $R^2$, trifluoromethane sulfonate, pyrrol-1-yl, optionally substituted with one or more of $R^2$, —NH—(CO)—$R^2$, —N($R^2$)$_2$, wherein $R^2$ is selected independently from one another, or non-coordinating anions.

When $X^2$ is a noncoordinating anion in the compound of Formula II, said anion is an anion being capable of stabilizing the respective cation in the compound of Formula II. Therefore, all anions are suitable having a low nucleophilic character such to not form a covalent bond between and $X^2$.

In a preferred embodiment, $X^2$ is selected from tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

Furthermore, if the compound of Formula II is provided in solution, as solvent in particular aprotic solvents are suitable, such as dimethyl formamide, dimethyl acetamide and dimethyl sulfoxide.

Y is oxygen, sulfur, N-adamantyl, N-tert-butyl, N—($C_{6-14}$)aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$.

$R^1$ and $R_1{}'$ are independently from one another H, linear or branched $C_1$ to $C_{18}$-alkyl or unsubstituted or substituted $C_6$ to $C_{14}$-aryl, wherein the substituents have the meaning of $R^2$.

In one embodiment, $R^1$ and $R_1{}'$ are independently from one another ortho-alkoxyphenyl, preferably wherein alkoxy is $C_1$ to $C_6$-alkoxy; or wherein $R^1$ and $R_1{}'$ are independently from one another H and ortho-alkoxyphenyl, preferably wherein alkoxy is $C_1$ to $C_6$-alkoxy.

In a preferred embodiment,
$A^1$ is $NR^2$ or $PR^2$;
$A^2$ is $CR^2R^{2'}$, $NR^2$, $PR^2$, O or S;
C is a carbene carbon atom;
ring B includes $A^1$-C-$A^2$ and is a unsubstituted or mono- or multisubstituted 5 to 7-membered ring, which may contain besides $A^1$ and $A^2$ further heteroatoms selected from nitrogen, phosphorus, oxygen or sulfur, and the substituents of which have the meaning of $R^2$;
$R^2$ and $R^{2'}$ are independently from one another H, a linear, a partially cyclic or branched $C_1$ to $C_{18}$-alkyl residue, a linear, a partially cyclic or branched $C_1$ to $C_{18}$-alkenyl residue, a $C_3$ to $C_{12}$-cycloalkyl residue, a linear, partially cyclic or branched $C_6$ to $C_{100}$-polyoxaalkyl residue, a $C_5$ to $C_{14}$-aryl or heteroaryl residue, a $C_3$ to $C_{14}$-aryloxy residue, a linear, partially cyclic or branched $C_1$ to $C_{18}$-perfluoroalkyl residue, a linear, partially cyclic or branched $C_1$ to $C_{18}$-perchloroalkyl residue, a linear, partially cyclic or branched partially fluorinated $C_1$ to $C_{18}$-alkyl residue, a partially chlorinated linear, partially cyclic or branched $C_1$ to $C_{18}$-alkyl residue, a perfluorinated or partially fluorinated $C_6$ to $C_{14}$-aryl residue, a perchlorinated or partially chlorinated $C_6$ to $C_{14}$-aryl residue;
and, when $A^1$ and $A^2$ are $NR^2$ or $PR^2$, respectively, $R^2$ may be the same or may be different, or
$R^2$ and $R^{2'}$ taken together form a linear or branched $C_1$ to $C_{18}$-alkylene residue;
M is Cr, Mo or W;
$X^1$ is a residue of a solid oxide, wherein the solid oxide is linked to M via oxygen;
$X^2$ is selected from the group comprising or consisting of $C_1$ to $C_{18}$-carboxylates, $C_1$ to $C_{18}$-alkoxides, fluorinated $C_1$ to $C_{18}$-alkoxides, $C_1$ to $C_{18}$ mono- or polyhalogenated carboxylates, unsubstituted, mono or multisubstituted $C_6$ to $C_{18}$-monophenolate, -biphenolate or -terphenolate, trifluoromethane sulfonate, non-coordinating anions, wherein the substituents at the monophenolate, bisphenolate or terphenolate have the meaning of halogen or $R^2$;
Y is oxygen, sulfur, N-adamantyl, N-tert-butyl, N—($C_{6-14}$) aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;
$R^1$ and $R^{1'}$ are independently from one another H, linear or branched $C_1$ to $C_{18}$-alkyl or unsubstituted or substituted $C_6$ to $C_{14}$-aryl, wherein the substituents have the meaning of $R^2$.

In a further preferred embodiment,
$A^1$ is $NR^2$ or $PR^2$;
$A^2$ is $CR^2R^{2'}$, $NR^2$, $PR^2$, O or S;
C is a carbene carbon atom;
ring B includes $A^1$-C-$A^2$ and is a unsubstituted or mono- or multisubstituted 5 to 7-membered ring, which may contain besides $A^1$ and $A^2$ further heteroatoms selected from nitrogen, phosphorus, oxygen or sulfur, and the substituents of which have the meaning of $R^2$;
$R^2$ and $R^{2'}$ are independently from one another H, a linear, a partially cyclic or branched $C_1$ to $C_{18}$-alkyl residue, a linear, a partially cyclic or branched $C_1$ to $C_{18}$-alkenyl residue, a $C_3$ to $C_{12}$-cycloalkyl residue, a linear, partially cyclic or branched $C_6$ to $C_{100}$-polyoxaalkyl residue, a $C_5$ to $C_{14}$-aryl or heteroaryl residue, a $C_3$ to $C_{14}$-aryloxy residue, a linear, partially cyclic or branched $C_1$ to $C_{18}$-perfluoroalkyl residue, a linear, partially cyclic or branched $C_1$ to $C_{18}$-perchloroalkyl residue, a linear, partially cyclic or branched partially fluorinated $C_1$ to $C_{18}$-alkyl residue, a partially chlorinated linear, partially cyclic or branched $C_1$ to $C_{18}$-alkyl residue, a perfluorinated or partially fluorinated $C_6$ to $C_{14}$-aryl residue, a perchlorinated or partially chlorinated $C_6$ to $C_{14}$-aryl residue;
and, when $A^1$ and $A^2$ are $NR^2$ or $PR^2$, respectively, $R^2$ may be the same or may be different, or
$R^2$ and $R^{2'}$ taken together form a linear or branched $C_1$ to $C_{18}$-alkylene residue;
M is Cr, Mo or W;
$X^1$ is a residue of a solid oxide, wherein the solid oxide is linked to M via oxygen;
$X^2$ in the compound of Formula I is selected from the group comprising or consisting of $C_1$ to $C_{18}$-carboxylates, $C_1$ to $C_{18}$-alkoxides, fluorinated $C_1$ to $C_{18}$-alkoxides, $C_1$ to $C_{18}$ mono- or polyhalogenated carboxylates, unsubstituted, mono or multisubstituted $C_6$ to $C_{18}$-monophenolate, -biphenolate or -terphenolate, trifluoromethane sulfonate, wherein the substituents at the monophenolate, bisphenolate or terphenolate have the meaning of halogen or $R^2$;
$X^2$ in the compound of Formula II is a noncoordinating anion, preferably selected from tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate;

Y is oxygen, sulfur, N-adamantyl, N-tert-butyl, N—($C_{6-14}$) aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;

$R^1$ and $R_1'$ are independently from one another H, linear or branched $C_1$ to $C_{18}$-alkyl or unsubstituted or substituted $C_6$ to $C_{14}$-aryl, wherein the substituents have the meaning of $R^2$; or $R^1$ and $R_1'$ are independently from one another ortho-alkoxyphenyl, preferably wherein alkoxy is $C_1$ to $C_6$-alkoxy; or wherein $R^1$ and $R_1'$ are independently from one another H and ortho-alkoxyphenyl, preferably wherein alkoxy is $C_1$ to $C_6$-alkoxy.

In another preferred embodiment, Y is oxygen. Thus, the catalysts according to the invention represent in one embodiment oxo alkylidene complexes such as tungsten oxo alkylidene complexes.

The moiety "=$CR^1R_1'$" in the compounds of Formula I and Formula II denotes an alkylidene group. In one embodiment, =$CR^1R_1'$ is selected from =CHC(CH$_3$)$_3$ or =CH(C(CH$_3$)$_2$C$_6$H$_5$.

In one embodiment, at least one of $R^1$ and $R_1'$ is ortho-alkoxyphenyl, preferably wherein alkoxy is $C_1$ to $C_6$-alkyl.

In a preferred embodiment, $R^1$ and $R_1'$ are independently from one another H and tert-butyl, or H and CMe$_2$Ph (Ph is phenyl). Thus, in one embodiment, $R^1$ is H and $R_1'$ is tert-butyl. In another embodiment, $R^1$ is tert-butyl and $R_1'$ is H. In one embodiment, $R^1$ is H and $R_1'$ is CMe$_2$Ph. In another embodiment, $R^1$ is CMe$_2$Ph and $R_1'$ is H.

In another preferred embodiment, $R^1$ and $R_1'$ are independently selected from one another from H and ortho-alkoxyphenyl, preferably wherein alkoxy is $C_1$ to $C_6$-alkyl.

Suitable alkoxy residues are preferably methoxy, ethoxy, and n- and iso-propoxy.

In still another preferred embodiment, ring B is a heterocycle as defined above with respect to a compound of Formula I or Formula II.

In one embodiment, said residue of said ring B is selected from the group comprising or consisting of: 1,3-disubstituted imidazol-2-ylidene, 1,3-disubstituted imidazolidin-2-ylidene, 1,3-disubstituted tetrahydropyrimidin-2-ylidene, 1,3-disubstituted diazepin-2-ylidene, 1,3-disubstituted dihydro-diazepin-2-ylidene, 1,3-disubstituted tetrahydrodiazepin-2-ylidene, N-substituted thiazol-2-ylidene, N-substituted thiazolin-2-ylidene, N-substituted triazol-2-ylidene, N-substituted dihydrotriazol-2-ylidene, mono- or multisubstituted triazolin-2-ylidene, N-substituted thiadiazol-2-ylidene, mono- or multisubstituted thiadiazolin-2-ylidene and mono- or multi-substituted tetrahydrotriazol-2-ylidene; wherein the heterocycle may have one or more further substituents, wherein said substituents independently have the meaning of $R^2$ or halogen or NR$^2$.

In a further preferred embodiment, ring B is selected from 1,3-dimesitylimidazol-2-ylidene, 1,3-dimesitylimidazolidin-2-ylidene, 1,3-di-tert-butylimidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridin-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,3,5,5-tetramethyl-1-mesityl-pyrrolidin-2-ylidene.

The catalyst according to the invention is heterogeneous, i.e. it comprises a solid support comprising a solid oxide.

In a preferred embodiment, the solid oxide is selected from the group comprising or consisting of: silica, titania, zirconia, cerium oxide, alumina, or a mixture of two or more thereof.

In a further preferred embodiment, the solid oxide is silica and $X^1$ is O—Si(O—)$_3$.

In other embodiments, the solid oxide is titania and $X^1$ is O—Ti(O—)$_3$, or zirconia and $X^1$ is O—Zr(O—)$_3$, or cerium oxide and $X^1$ is O—Ce(O—)$_3$ or O—Ce(O—)$_2$, or aluminum oxide and $X^1$ is O—Al(O—)$_2$. In a further preferred embodiment, the oxide, preferably silica, is comprised in a solid support.

In one embodiment,

M is selected from Mo or W;

Y is selected from oxygen, sulfur, N-adamantyl, N-tert-butyl, N—($C_{6-14}$)aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;

ring B is selected from 1,3-dimesitylimidazol-2-ylidene, 1,3-dimesitylimidazolidin-2-ylidene, 1,3-di-tert-butylimidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene;

$R^1$ and $R_1'$ are independently from one another H and tert-butyl, or H and CMe$_2$Ph; or wherein at least one of $R^1$ and $R_1'$ is ortho-alkoxyphenyl, preferably wherein alkoxy is $C_1$ to $C_6$-alkyl; or wherein $R^1$ and $R_1'$ are independently from one another H and ortho-alkoxyphenyl, preferably wherein alkoxy is $C_1$ to $C_6$-alkyl;

$X^1$ is (—O—)$_3$Si—O—; and $X^2$ is selected from the group comprising or consisting of halide, preferably F and Cl, $C_1$ to $C_{18}$-carboxylates, $C_1$ to $C_{18}$-alkoxides, fluorinated $C_1$ to $C_{18}$-alkoxides, $C_1$ to $C_{18}$-mono- or polyhalogenated carboxylates, unsubstituted, mono or multisubstituted $C_6$ to $C_{18}$-monophenolate, -biphenolate or -terphenolate, trifluoromethane sulfonate, wherein the substituents at the monophenolate, bisphenolate or terphenolate have the meaning of halogen or $R^2$; and tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

In one embodiment,

M is selected from Mo or W;

Y is selected from oxygen, N-adamantyl, N-tert-butyl, N—($C_{6-14}$)aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;

ring B is selected from 1,3-dimesitylimidazol-2-ylidene, 1,3-dimesitylimidazolidin-2-ylidene, 1,3-di-tert-butylimidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene;

$R^1$ and $R_1'$ are independently from one another H and tert-butyl, or H and $CMe_2Ph$; or wherein at least one of $R^1$ and $R_1'$ is ortho-alkoxyphenyl, preferably wherein alkoxy is $C_1$ to $C_6$-alkyl; or wherein $R^1$ and $R_1'$ are independently from one another H and ortho-alkoxyphenyl, preferably wherein alkoxy is $C_1$ to $C_6$-alkyl;

$X^1$ is $(-O-)_3Si-O-$; and $X^2$ is selected from the group comprising or consisting of F and Cl, trifluoromethane sulfonate, tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

The following table exhibits some preferred embodiments [OTf=triflate; $B(Ar^F)_4$=tetrakis(3,5-bis(trifluoromethyl)phenyl)borate; $B(C_6F_5)_4$=tetrakis(pentafluorophenyl)borat; Me=methyl, Ph=phenyl; ≡SiO is $(-O-)_3Si-O-$)]

| # | M | Ring B | $CR^1R^{1'}$ | $X^1$ | $X^2$ | Y |
|---|---|---|---|---|---|---|
| 1@SiO$_2$ | W | 1,3-dimesitylimidazol-2-ylidene (IMes) | =CHCMe$_2$Ph | ≡SiO | OTf | O |
| 2@SiO$_2$ | W | 1,3-dimesitylimidazol-2-ylidene | =CHCMe$_2$Ph | ≡SiO | B(Ar$^F$)$_4$ | O |
| 3@SiO$_2$ | W | 4,5-dichloro-1,3-dimethyl-imidazol-2-ylidene | =CHCMe$_3$ | ≡SiO | Cl | N$^t$Bu |
| 4@SiO$_2$ | W | 4,5-dichloro-1,3-dimethyl-imidazol-2-ylidene | =CHCMe$_3$ | ≡SiO | Al[OC(CF$_3$)$_3$]$_4$ | N$^t$Bu |
| 5@SiO$_2$ | W | 1,3,5-Ph$_3$-triazol-2-ylidene | =CHCMe$_2$Ph | ≡SiO | B(Ar$^F$)$_4$ | O |
| 6@SiO$_2$ | Mo | 1,3,5-Ph$_3$-triazol-2-ylidene | =CHCMe$_2$Ph | ≡SiO | B(Ar$^F$)$_4$ | N-2,6-Cl$_2$—C$_6$H$_3$ |
| 7@SiO$_2$ | Mo | 1,3,5-Ph$_3$-triazol-2-ylidene | =CHCMe$_2$Ph | ≡SiO | B(Ar$^F$)$_4$ | N-2-CF$_3$—C$_6$H$_4$ |
| 8@SiO$_2$ | Mo | 1,3,5-Ph$_3$-triazol-2-ylidene | =CHCMe$_2$Ph | ≡SiO | B(Ar$^F$)$_4$ | N-3,5-Me$_2$—C$_6$H$_3$ |
| 9@SiO2 | Mo | 1,3-dimesitylimidazol-2-ylidene | =CHCMe$_2$Ph | ≡SiO | B(Ar$^F$)$_4$ | N-2,6-Me$_2$—C$_6$H$_3$ |
| 10@SiO$_2$ | Mo | 1,3-dimesitylimidazolidin-2-ylidene (H$_2$IMes) | =CHCMe$_2$Ph | ≡SiO | B(Ar$^F$)$_4$ | N-2,6-Me$_2$—C$_6$H$_3$ |
| 11@SiO$_2$ | W | 1,3-dimesitylimidazol-2-ylidene | =CH-(2-methoxyphenyl) | ≡SiO | B(Ar$^F$)$_4$ | O |
| 12@SiO$_2$ | Mo | 1,3-dimesitylimidazolidin-2-ylidene | =CH-(2-methoxyphenyl) | ≡SiO | B(Ar$^F$)$_4$ | N-2,6-Me$_2$—C$_6$H$_3$ |
| 13@SiO$_2$ | Mo | 1,3-dimesitylimidazol-2-ylidene | =CH-(2-methoxyphenyl) | ≡SiO | B(Ar$^F$)$_4$ | N-2,6-Me$_2$—C$_6$H$_3$ |
| 14@SiO$_2$ | Mo | 1,3-dimesitylimidazol-2-ylidene | =CHCMe$_2$Ph | ≡SiO | B(Ar$^F$)$_4$ | N-2-tert-butyl C$_6$H$_4$ |
| 15@SiO2 | W | 1,3-dimesitylimidazol-2-ylidene | =CHCMe$_2$Ph | ≡SiO | B(C$_6$F$_5$)$_4$ | O |

[Compounds in which $X^2 = B(Ar^F)_4$ or $B(C_6F_5)_4$ fall under the general Formula II]

from one another H and ortho-alkoxyphenyl, preferably wherein alkoxy is $C_1$ to $C_6$-alkyl;

$X^1$ is $(-O-)_3Si-O-$; and $X^2$ is selected from the group comprising or consisting of F and Cl, $C_1$ to $C_{18}$-alkoxides, fluorinated $C_1$ to $C_{18}$-alkoxides, trifluoromethane sulfonate, tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

In one embodiment,

M is selected from Mo or W;

Y is selected from oxygen, N-adamantyl, N-tert-butyl, N—(C$_{6-14}$)aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;

ring B is selected from 1,3-dimesitylimidazol-2-ylidene, 1,3-dimesitylimidazolidin-2-ylidene, 1,3-di-tert-butylimidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene;

$R^1$ and $R_1'$ are independently from one another H and tert-butyl, or H and $CMe_2Ph$; or wherein at least one of $R^1$ and $R_1'$ is ortho-alkoxyphenyl, preferably wherein alkoxy is $C_1$ to $C_6$-alkyl; or wherein $R^1$ and $R_1'$ are independently from one another H and ortho-alkoxyphenyl, preferably wherein alkoxy is $C_1$ to $C_6$-alkyl;

The compounds of general Formula I and general Formula II may further contain a neutral ligand. Neutral ligands are e.g. selected from nitriles such as acetonitrile or benzonitrile, phosphines such as trimethylphosphine or dimethylphenylphosphine, and ethers such as tetrahydrofuran.

Second Aspect: Method of Making the Compounds According to the Invention

According to a second aspect, the invention relates to a method of making a compound of the general Formula I or II as defined in the first aspect, or any embodiment defined therein, comprising at least the following step (S):

(S) reacting a solid oxide with a compound of the general Formula III or IV

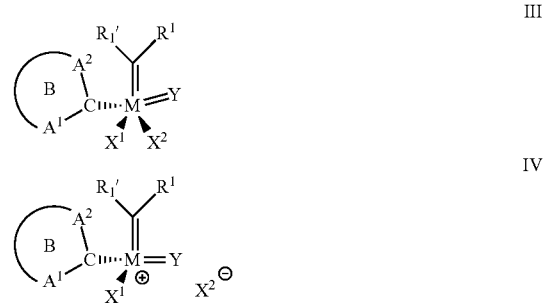

wherein, $A^1$, $A^2$, C, ring B, $X^2$, $R^1$ and $R^1$ have the meaning as defined in the first aspect with respect to compounds of general Formula I and II.

$X^1$ as used with respect to the method according to the second aspect, contrary to the meaning as used with regard to the compounds according to the first aspect, may be any group which is capable of being replaced by an oxygen atom of the solid oxide, respectively the residue of the solid oxide. Thus, in its broadest meaning, $X^1$ denotes a leaving group.

Basically, all leaving groups may be employed as $X^1$ such as a $C_{0-8}$ sulfonate such as fluorosulfonate ($FSO_2O$), triflate ($CF_3SO_2O$), nonaflate ($C_4F_9SO_2O$), mesylate ($CH_3SO_2O$), tosylate (p-$CH_3C_6H_4SO_2O$), halogenide such as chloride, bromide and iodide, nitrate and phosphate and $C_{1-8}$ esters of phosphate, alcoholate such as fluorine-containing $C_{1-8}$ alcoholates such as $(CF_3)(CH_3)CH-O$, $(CF_3)_2CH-O$ or $(CF_3)_3C-O$, or phenolates such as $C_6F_5-O$.

In one embodiment, $X^1$ is sulfonate, preferably a fluorine-containing $C_{0-8}$ sulfonate.

In one embodiment, $X^1$ is selected from the group comprising or consisting of: $FSO_2O$, $CF_3SO_2O$, $C_4F_9SO_2O$, $CH_3SO_2O$, p-$CH_3C_6H_4SC_2O$, $(CF_3)(CH_3)CH-O$, $(CF_3)_2CH-O$, $(CF_3)_3C-O$ and $C_6F_5-O$.

In another embodiment, $X^1$ is $C_{1-8}$ alcoholate, preferably a fluorine-containing $C_{1-8}$ alcoholate.

In a particular preferred embodiment, $X^1$ is selected from $(CF_3)(CH_3)CH-O$, $(CF_3)_2CH-O$ and $(CF_3)_3C-O$.

In another preferred embodiment, $X^1$ is $C_6F_5-O$.

The compounds of Formula III and IV as used as starting materials in the method according to the invention as defined in the second aspect for making the compounds of Formula I and II according to the invention as defined in the first aspect are known or may be prepared according to known methods.

The hydroxyl content of the solid oxide in step (S) may be freely selected depending on drying temperature and drying time. Accordingly, the solid oxides used for making the compounds of Formula I and of Formula II according to the invention may be adjusted in a tailor-made manner to the required properties of the alkylidene compound to be immobilized. In this regard it is noteworthy that depending on the number of mmol of hydroxyl groups per gram solid oxide, the amount of alkylidene compound per gram of solid oxide and ultimately the activity of the resulting catalyst may be adjusted depending upon needs.

Preferably, prior to step (S), the solid oxide, preferably silica, is heated in a temperature range of from 150 to 1,000° C., preferably employing vacuum or a flow of dry air or inert gas such as nitrogen or argon.

Accordingly, the method as defined in the second aspect further comprises (R) prior to step (S):
(R): heating the solid oxide.

In a further preferred embodiment, the solid oxide, preferably silica, is subjected to a temperature in the range of from 300 to 800° C. under pressure ranging from $10^{-6}$ mbar to 1 bar or a flow of dry air or inert gas such as nitrogen or argon, preferably for a period ranging from 4 to 24 h. Temperature and pressure may be performed in ramps.

Preferably, hydroxyl content determined by means of titration with MeMgCl ranges from 0.05 mmol to 2.00 mmol per g solid oxide, preferably silica, further preferred from 0.1 mmol to 2 mmol per g solid oxide.

Exemplarily, in one embodiment, silica is partially dehydroxylated and dehydrated at 700° C. ($SiO_{2-(700)}$).

However, other temperatures or temperature ranges may also be used depending on the requirements of the catalyst to be prepared and to be used as heterogeneous catalyst.

Thus, preferably, a silica is used in the method according to the invention which is partially dehydroxylated and dehydrated. Preferably, silica is dehydroxylated and dehydrated at elevated temperature, preferably at elevated temperature and in vacuo or a flow of dry air or inert gas such as nitrogen or argon. The term "relative low temperatures" relates to a temperature range of from 150 to 300° C., preferably 180 to 250° C., more preferably 200° C. The term "relative high temperatures" relates to a temperature range of 400 to 1,000° C., preferably 600 to 800° C., more preferably 700° C. The term "medium temperatures" preferably relates to a temperature range of from 200 to 600° C., more preferably 300 to 500° C.

Accordingly, in one embodiment, the method comprises at least step (R.1) or (R.2) or (R.3) prior to step (S):
(R.1) heating silica or heating silica in vacuo; or
(R.2) heating silica or heating silica in vacuo or heating silica in a flow of dry air or inert gas in a temperature range of from 150° C. to 300° C.; or
(R.3) heating silica or heating silica in vacuo or heating silica in a flow of dry air or inert gas in a temperature range of from 600° C. to 800° C.

Alternatively, the method comprises at least step (R.4):
(R.4) calcining silica at 500° C., rehydrating the calcined product at 200° C., and dehydroxylating the rehydrated product at 200° C. or higher.

The reaction of a compound of Formula III or Formula IV with a solid oxide such as silica is preferably performed in an organic solvent for the compound.

In case of a compound of Formula III as starting material, solvents such as an aromatic solvent may be used, e.g. benzene or toluene.

In case of a compound of Formula IV as starting material, an aprotic solvent is used such as the aprotic solvents mentioned before.

The reaction may be performed at ambient temperature such as 20 to 30° C.

In one embodiment, when a mixture of a compound of Formula III or IV, solid support and solvent are stirred for a period of time in the range of from 2 to 10 hours, the reaction is terminated.

The reaction may be controlled by solution NMR while quantifying the released leaving group in its protonated form, e.g. released $tBu_{F6}OH$.

Subsequently, the formed target compound of Formula I or Formula II may be isolated by filtration.

Figure 1:
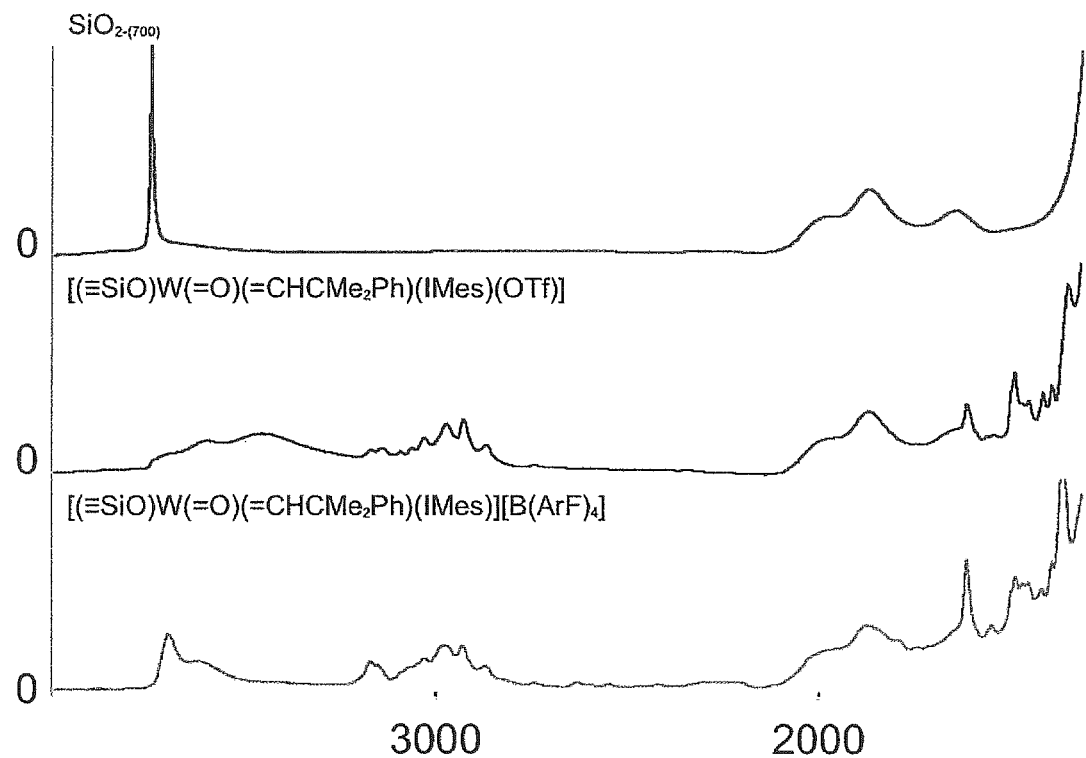
FIG. 1 shows the transmission FTIR spectra of compounds 1@SiO$_2$ and 2@SiO$_2$ according to the invention compared to the FTIR spectra of SiO$_{2\text{-}(700)}$. The X-axis denotes the wavenumbers (cm$^{-1}$) and the y-axis the absorption.

The metal content in terms of M in the isolated compound of Formula I or II may be determined by elemental analysis. The presence of e.g. residual silanol may be determined by means of e.g. infrared spectroscopy such as FTIR. Commonly, a significant decrease in the intensity of the isolated silanol stretch at 3647 $cm^{-1}$ with respect to $SiO_{2-(700)}$ may be observed, broad bands centered at 3590 $cm^{-1}$ and 2500 $cm^{-1}$ appeared in the spectra, besides $v_{CH}$ and $\delta_{CH}$ bands associated with the organic ligands between 3500 $cm^{-1}$ and 2500 $cm^{-1}$. The broad bad can be associated to residual surface silanols interacting with nearby aromatic residues, consistent with a partial grafting of these relatively large molecules (see FIG. 1)

The following scheme exemplarily shows the preparation of compounds $1@SiO_{2-(700)}$ and $2@SiO_{2-(700)}$:

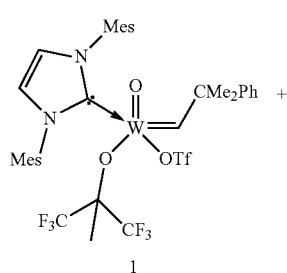

1

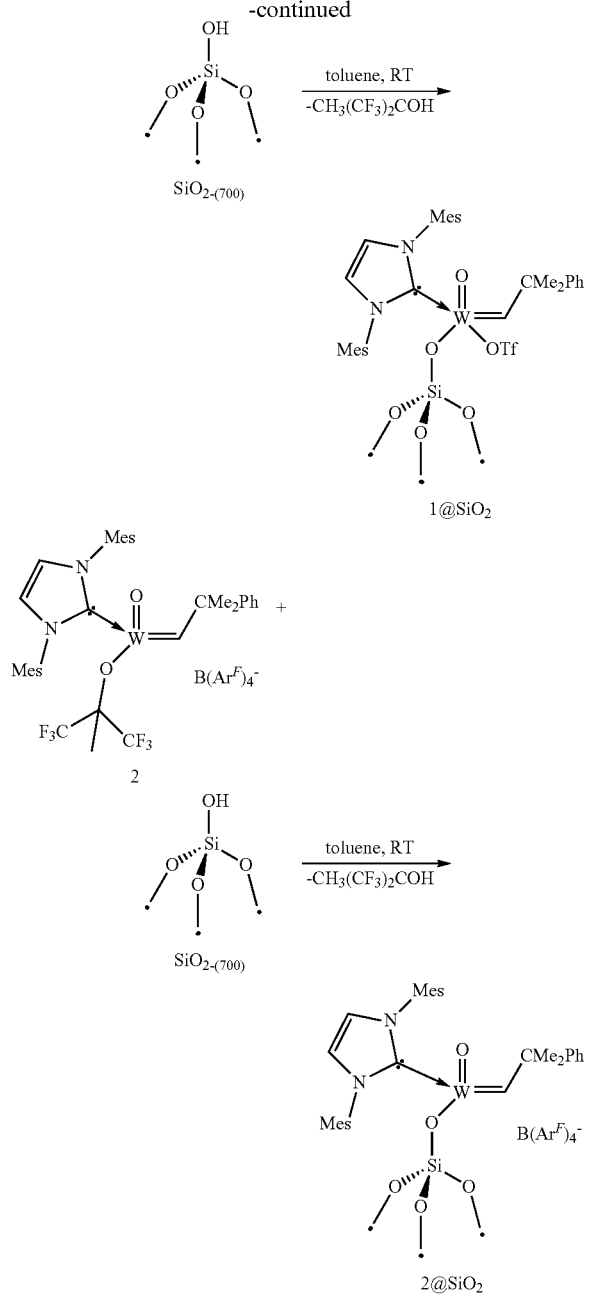

Third Aspect: Metathesis Reactions Using the Compounds According to the Invention The compounds defined in the first aspect may be used for reacting compounds having an olefinic double bond in a metathesis reaction.

Accordingly, the invention further relates to a method of forming an olefin from a first and a second olefin in a metathesis reaction, comprising step (T):

(T) reacting the first olefin with the second olefin in the presence of a compound of general Formula I or II as defined in the first aspect, or made according to a method as defined in the second aspect, wherein the first and the second olefin may be the same or may be different from one another.

In one embodiment, the first and the second olefin or the first and the second olefin may bear one or more functional groups.

Preferably, the first and the second olefin or the first or the second olefin may bear one or more functional groups independently selected from the group consisting of ether, ester, amide, amine, halogen, nitrile, thioether, thioester, aryl, or heteroaryl.

In a further preferred embodiment, the first and the second olefin or the first or the second olefin bear one or more functional groups independently selected from alkoxy, aryloxy, perhaloalkoxy, arylalkoxy, heteroaryl, heteroaryloxy, heteroarylalkyl, heteroarylalkoxy, amino, halogen, alkylthio, oxo, carboxy esters, carboxamido, acyloxy, aminoalkyl, alkylaminoaryl, alkylaminoalkyl, alkoxyaryl, arylamino, arylalkylamino, alkylsulfonyl, carboxamidoalkylaryl, carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl.

The structure of the first and the second olefin may be vastly freely selected.

Preferably,
(a) the first olefin and the second olefin are identical [homo or self-metathesis (SM)]; or
(b) the first and the second olefin are different from one another [cross metathesis (CM)]; or
(c) the first olefin has an internal olefinic double bond and the second olefin is ethylene [ethenolysis]; or
(d) the first olefin is a cyclic olefin and the second olefin is a cyclic olefin, wherein the first and the second olefin may be identical or may be different from one another [cross metathesis (SM) or (CM)]; or
(e) the first olefin is a diene and the second olefin is a diene, wherein the first olefin and the second olefin are identical, wherein step (i) results in the ring closing of the diene [ring closing metathesis (RCM)]; respectively the first and the second olefin are in the same molecule; or
(f) the first olefin is a cyclic olefin and the second olefin is a cyclic olefin, wherein the first olefin and the second olefin are identical, wherein step (i) results in a ring opening metathesis polymerization (ROMP); or
(g) the first olefin is a cyclic olefin and the second olefin is a cyclic olefin, wherein the first olefin and the second olefin are identical, wherein step (i) results in a ring opening metathesis followed by a ring-closing metathesis reaction (ROM-RCM);
(h) the first olefin is a terminal diene and the second olefin is a terminal diene, wherein the first olefin and the second olefin are identical, and wherein step (i) results in a acyclic diene metathesis polymerization (ADMET), wherein a polyene and ethylene are generated.

Preferably, the method according to step (T) is carried out in a solvent, which dissolves the olefins and suspends the catalyst. Suitable solvents are solvents selected from aromatic solvents, preferably toluene, halogenated solvents, preferably chlorobenzene or methylene dichloride, alkanes, preferably pentane or hexane or octane. However, step (T) may be carried out without solvent, preferably if one of the olefins is a liquid under the reaction conditions. A reaction of the first and the second olefin in gaseous phase is likewise possible or the first olefin is in gaseous phase and the second olefin is in liquid phase.

The temperature employed in step (T) preferably ranges from −20° C. to 250° C., more preferably from 0° C. to 110° C., still more preferably from 15 to 50° C.

However, if necessary, the compounds according to the invention may also be employed at rather high temperatures such as 150° C. or above.

The concentration of the compound according to the invention used as catalyst in the method according to the invention can vary in broad ranges. Preferably, the catalyst is employed in a molar ratio of <5 mol % (calculated in terms of M), based on the first or the second olefin (100 mole %).

In a preferred embodiment, the formation of the E-olefin is preferred over the formation of the Z-olefin, i.e. the metathesis reaction employing the catalysts according to the invention shows a high E/Z-selectivity.

The proceeding of the reaction may be controlled preferably by gas or liquid chromatographic methods eventually coupled to Mass Spectrometry.

Preferably, the reaction is terminated by separating off the catalyst from the reaction mixture obtained in step (S). Separating off may be performed by methods such as filtration or centrifugation or distilling off the reaction mixture from the catalyst.

It has been surprisingly found that the compounds according to the invention after the separating off may be re-used in the reaction according to step (S) without considerable loss of activity and selectivity. This makes the compounds according to the invention particularly advantageous over respective homogeneous catalysts, which frequently require a complex processing of the reaction mixture obtained from metathesis, wherein the catalysts are often destroyed or at least considerably deteriorated in their activity.

Thus, the compounds according to the invention perform particularly beneficial at an industrial scale.

Accordingly, in one embodiment, the method according to the invention further comprises at least step (T.1) or step (T.1) and step (T.2):

(T.1) separating off the compound according to the invention from the reaction mixture obtained in step (T), preferably by filtration or centrifugation or distilling off the reaction mixture from the compound according to the invention;

(T.2) re-using in step (T) the catalyst obtained in step (T.1).

Thus, in general, the invention further relates to the use of a compound as defined in the first aspect in a metathesis reaction.

Preferably, the metathesis reaction is selected from the group consisting of self-metathesis (SM), cross metathesis (CM), ring opening metathesis (ROM), ring closing metathesis (RCM), ROM-RCM, ring opening metathesis polymerization (ROMP), ethenolysis, and acyclic diene metathesis polymerization (ADMET).

Fourth Aspect: Method of Converting a Compound According to the Invention into Another Compound According to the Invention In a fourth aspect, the invention relates to a method in which an oxide supported metal complex, preferably a silica supported metal complex according to the invention is converted into another oxide supported metal complex, preferably a silica supported complex according to the invention by reacting said oxide supported complex, preferably a silica supported complex of general Formula I or general Formula II with a styrene.

Accordingly, in a fourth aspect, the invention relates to a method of converting a compound of general Formula I or general Formula II as defined in the first aspect into a compound of general Formula VI or general Formula VII, comprising at least step (U):

(U): reacting said compound of general Formula I with a compound of general Formula V to yield said compound of general Formula VI, or reacting said compound of general Formula II with a compound of general Formula V to yield said compound of general Formula VII,

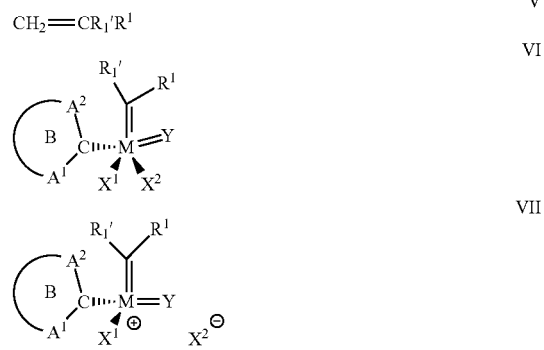

wherein at least one of $R_1'$ and $R^1$ in the compound of Formula V is different from at least one of $R_1'$ and $R^1$ as defined in general Formula I or general Formula II, and wherein $R_1'$ and $R^1$ in general Formula VI and general Formula VII have the same meaning as in general Formula V.

Accordingly, the method provides for an exchange of the respective $=CR_1'R^1$-moiety, i.e. the exchange of the alkylidene moiety by another (different) alkylidene moiety.

The reaction according to step (U) generally is carried out in a solvent. Suitable solvents preferably are aromatics such as benzene or toluene.

Preferably, the reaction proceeds in a temperature range of from 0° C. to 100° C., more preferably 10 to 50° C.

The reaction time is preferably within 1 to 4 h.

Preferably, a molar excess of compound V relative to the compound of general Formula VI or VII is used.

In a preferred embodiment, compound V is a styrene derivative which bears an alkoxy residue in 2-position, i.e. in ortho position to the $CH_2=CH-$ group. Said alkoxy residue preferably is a $C_1$ to $C_6$ alkoxy group. Suitable alkoxy residues are preferably methoxy, ethoxy, and n- and iso-propoxy.

Compounds according to the invention in which at least one of $R^1$ and $R_1'$ is ortho-alkoxyphenyl, or wherein $R^1$ and $R_1'$ are independently from one another H and ortho-alkoxyphenyl, preferably have a better temperature stability compared to respective compounds according to the invention not bearing such an ortho-alkoxyphenyl group.

For example, compound 2@$SiO_2$ may be converted into compound 11@$SiO_2$ by reacting compound 2@$SiO_2$ with o-methoxystyrene.

In another example, compound 9@$SiO_2$ may be converted into compound 13@$SiO_2$ by reacting compound 9@$SiO_2$ with o-methoxystyrene.

In another example, compound 10@$SiO_2$ may be converted into compound 12@$SiO_2$ by reacting compound 10@$SiO_2$ with o-methoxystyrene.

EXAMPLES

General Considerations

For the synthesis of the molecular precursors all experiments were carried out under dry and oxygen free nitrogen atmosphere using an MBraun glove-box. For the supported complexes, reactions were carried out using high vacuum lines ($10^{-5}$ mbar) and glove-box techniques.

Solvents. Pentane, diethyl ether, methylene chloride, THF and toluene were purified using double MBraun SPS alumina columns. Benzene, heptane and benzene-$d_6$ were distilled from Na/benzophenone and degassed by three consecutive freeze-pump-thaw cycles. For intermediates of 9-13@$SiO_2$ benzene, toluene, and pentane were distilled from potassium. Dichloromethane were distilled from calcium hydride. Acetonitrile was further purified by percolation through aluminum oxide 90 active basic (Merck).

Substrates and internal standards. Octadecane was distilled under partial pressure; 1-nonene, cis-4-nonene, diallyldiphenylsilane and diallyl ether were distilled from Na, degassed by three consecutive freeze-pump-thaw cycles and stored for 5 hours over activated Selexsorb CD®. Ethyl oleate was degassed by three consecutive freeze-pump-thaw cycles and stored for 5 hours over activated Selexsorb CD®. Propene was purified using a Gasclean CC-X column (Nikka Seiko Co. LTD.). 9-DDAME was purified by percolation through 20 weight-% aluminium oxide 90 active basic (Merck) under the atmosphere of the glovebox (repeated 3 times).

Silica. Silica (Aerosil Degussa, 200 $m^2$ $g^{-1}$) was compacted with distilled water, sieved, calcined at 500° C. under air for 4 h and treated under vacuum ($10^{-5}$ mbar) at 500° C. for 12 h and then at 700° C. for 12 h (support referred to as $SiO_{2-700}$).

IR and NMR. All infrared (IR) spectra were recorded using a Bruker FT-IR Alpha spectrometer placed in the glovebox, equipped with OPUS software. Spectral range 275-7500, resolution <2 $cm^{-1}$, RockSolid interferometer, DTGS (triglycine sulfate) detector, SiC globar source, solid samples were investigated in a magnetic pellet holder. A typical experiment consisted of the measurement of transmission in 32 scans in the region from 4000 to 400 $cm^{-1}$. Solution $^1H$ and $^{13}C$-NMR spectra were obtained on Bruker DRX 300, DRX 250, DRX 500 or Bruker Avance III or Bruker Avance 300 spectrometers in methylene chloride-$d_2$ or benzene-$d_6$ at room temperature. The $^1H$ and $^{13}C$ chemical shifts are referenced relative to the residual solvent peak.

Flow reactor. Propene metathesis was investigated in flow conditions using a PID Eng. & Tech. Microactivity Reference flow reactor. The output gas composition was analyzed with a GC-FID chromatograph.

Batch ethenolysis experiments. The ethenolysis of ethyl oleate was conducted in an Endeavor parallel autoclave operated inside a nitrogen filled glovebox (<0.5 ppm $H_2O$ and $O_2$). The autoclave contains eight reactors equipped with glass liners. Samples were taken outside the glovebox, quenched with wet ethyl acetate and analyzed by GC, see below.

Gas Chromatography. Liquid catalytic test aliquots were analyzed using a GC/FID (Agilent Technologies 7890 A) equipped with a split-splitless injector heated to 250° C., injection volume 0.5 mikroL and hydrogen carrier gas. Chromatographic separations for 1-nonene and cis-4-nonene catalytic tests were performed using an HP-5 (Agilent Technologies) column (30 m, 0.32 mm, 0.25 mikrom stationary phase). Chromatographic separation for ethyl oleate catalytic tests and ethenolysis test were performed using an HP88 (Agilent Technologies) column (30 m, 0.25 mm, 0.20 mikrom stationary phase). Homo metathesis of 9-DDAME was monitored by GCMS analysis. GC spectra were performed on a Shimadzu GC-2010 Plus column (Zebron ZB-35HT Inferno 30 m), and MS spectra were recorded on a GCMS_QP 2010 Ultra instrument.

Propene metathesis output gases from a flow reactor were analyzed using a GC/FID (Agilent Technologies 7890 A) equipped with a split-splitless injector heated at 200° C., He carrier gas and DB1 (Agilent J&W) and GS-gaspro (Agilent J&W) columns mounted in series.

Elemental Analyses were performed in Mikroanalytisches Labor Pascher, Germany. For molecular precursors: Institut für Anorganische Chemie, University of Stuttgart, Germany.

Synthesis of [Unsaturated (Wes)] Molecular Precursors for Compounds According to the Invention Synthesis of W(O)(CHCMe$_2$Ph)(IMes)(OCCH$_3$(CF$_3$)$_2$)(Otf), 1 [IMes=1,2-dimesitylimidazol-2-ylidene]

W(O)(CHCMe$_2$Ph)(IMes)(OCCH$_3$(CF$_3$)$_2$)(Cl) (Schowner, R.; Frey, W.; Buchmeiser, M. R. *J. Am. Chem. Soc.* 2015, 137, 6188) (49,5 mg, 0.058 mmol, 1 equiv.) was dissolved in 5 mL dichloromethane and cooled to −40° C. for 30 min. To the cold solution was added solid silver triflate (15 mg, 0.058 mmol, 1 equiv.) portion wise under vigorous stirring. A colorless precipitate of AgCl formed immediately. The suspension was stirred for 1 h under the exclusion of light. Subsequently the solid was filtered off over celite and the solvent was removed in vacuo to yield a yellow oil. The oil was redissolved and filtered several times to remove residual silver salts. The yellow oil was triturated with hexane until a pale yellow solid formed. The solid was filtered off and washed with hexane to yield the product (41.5 mg, 74%). $^1H$ NMR (400 MHz, CD$_2$Cl$_2$): δ=10.69 (s, $^1J_{C-H}$=120.2 Hz, 1H, W=CH), 7.27 (s, 2H, N—CH=CH—N), 7.18 (m, 4H, Ar), 7.08 (m, 1H, Ar), 7.03 (s, 2H, Mes-Ar), 6.96 (s, 2H, Mes-Ar), 2.31 (s, 6H, Mes-Me), 2.18 (s, 6H, Mes-Me), 2.13 (s, 6H, Mes-Me), 1.45 (s, 3H, CMe$_2$Ph), 0.81 (m, br, 3H, CMe(CF$_3$)$_2$), 0.74 (s, 3H, CMe$_2$Ph); $^{13}C$ NMR (100 MHz, CD$_2$Cl$_2$): δ=278.2 (W=C), 186.0 (N—C—N), 150.9 (CMe$_2$Ph), 141.7 (ipso-Mes), 137.1 (o-Mes), 136.4 (m-Mes), 130.4 (p-Mes), 128.6, 128.5 (m-CMe$_2$Ph), 126.5 (o-CMe$_2$Ph), 126.1 (p-CMe$_2$Ph), 125.8 (N—CH=CH—N), 82.3 (m, CMe(CF$_3$)$_2$), 50.8 (CMe$_2$Ph), 29.9 (CMe$_2$Ph), 29.0 (CMe$_2$Ph), 21.3 (p-Mes-Me), 18.5 (o-Mes-Me), 18.4 (o-Mes-Me), 17.6 (OCMe(CF$_3$)$_2$); $^{19}F$ NMR (375 MHz, CD$_2$Cl$_2$): δ=−77.71 (OTf), −77.76 (CF$_3$). Anal. calcd. for C$_{36}$H$_{39}$F$_9$N$_2$O$_5$SW: C, 44.73; H, 4.07; N, 2.90. Found: C, 44.67; H, 4.195; N, 2.98.

Synthesis of [W(O)(CHCMe$_2$Ph)(IMes)(OCCH$_3$(CF$_3$)$_2$)][B(Ar)$_4$], 2

This compound was previously reported (Schowner, R.; Frey, W.; Buchmeiser, M. R. *J. Am. Chem. Soc.* 2015, 137, 6188). Procedure and data is given for convenience.

W(O)(CHCMe$_2$Ph)(IMes)(OCCH$_3$(CF$_3$)$_2$)(Cl) (Schowner, R.; Frey, W.; Buchmeiser, M. R. *J. Am. Chem. Soc.* 2015, 137, 6188) (32 mg, 0.0375 mmol) was dissolved in 5 mL of CH$_2$Cl$_2$ and cooled at −40° C. for 30 min. The solution was added to solid NaB(Ar$^F$)$_4$ (33.3 mg, 1 equiv.) The suspension was stirred for 30 min. A colorless precipitate formed. Then the solution was cooled at −40° C. for 30 min and filtered through a glass fiber filter. The filtrate was reduced in vacuo to one third of the volume and filtered again. After removing the solvent an oily foam formed. It was triturated with pentane until a bright orange solid precipitated. The pentane phase was decanted and the solid was dried in vacuo. Yield 55 mg (87%). $^1H$ NMR (400 MHz, CD$_2$Cl$_2$): δ=10.52 (s, $^1J_{C-H}$=123.3 Hz, 1H, W=CH), 7.74 (m, br, 8H, BAr$^F$), 7.68 (s, 2H, N—CH=CH—N), 7.57 (s, br, 4H, BAr$^F$), 7.18-7.31 (m, 5H, Ar), 7.16 (s, br, 2H, Mes-Ar), 7.02 (s, br, 2H, Mes-Ar), 2.37 (s, 6H, Mes-Me), 2.05 (s, 6H, Mes-Me), 1.94 (s, 6H, Mes-Me), 1.64 (s, 3H, CMe$_2$Ph), 1.32 (sept, 3H, CMe(CF$_3$)$_2$), 1.29 (s, 3H, CMe$_2$Ph); $^{13}$C NMR (100 MHz, CD$_2$Cl$_2$): δ=297.3 (W=C), 181.8 (N—C—N), 162.4 (q, J$_{C-B}$=49.8 Hz, 4xBC(BAr$^F$)), 147.6 (ipso-CMe$_2$Ph), 143.6 (ipso-Mes), 135.4 (s, br, 4x2C, o-CH (BAr$^F$)), 135.3 (p-Mes), 134.3 (o-Mes), 133.0 (o-Mes), 131.2 (m-Mes), 131.1 (m-Mes), 129.5 (qq, J$_{C-F}$=31.6 Hz, J$_{C-B}$=2.7 Hz, 4xC—CF$_3$ (BAr$^F$)), 129.4 (m-Ar), 128.6 (p-Ar), 127.9 (o-Ar), 126.3 (N—CH=CH—N), 123.8 (q, J$_{C-F}$=273.4 Hz, 4x2CF$_3$ (BAr$^F$)), 118.1 (sept, J$_{C-F}$=3.8 Hz, p-CH (BAr$^F$)), 86.3 (m, OCMe(CF$_3$)$_2$), 52.7 (CMe$_2$Ph), 31.9 (CMe$_2$Ph), 29.4 (CMe$_2$Ph), 21.5 (p-Mes-Me), 19.3 (OCMe(CF$_3$)$_2$), 17.9 (o-Mes-Me), 17.8 (o-Mes-Me); $^{19}$F NMR (375 MHz, CD$_2$Cl$_2$): δ=−62.86 (BAr$^F$), −78.61 (OCMe(CF$_3$)$_2$). Anal. Calcd. for C$_{67}$H$_{51}$BF$_{30}$N$_2$O$_2$W: C, 47.88; H, 3.06; N, 1.67. Found: C, 47.96; H, 3.279; N, 1.84.

Synthesis of $^{13}$C Dilabeled Complexes $^{13}$C-labeled 1,3-dimesitylimidazolium chloride was prepared according to a known procedure (Hintermann, L. *Beilstein J. Org. Chem.* 2007, 3, No. 22) using a $^{13}$C enriched formaldehyde solution (20% in H$_2$O) yielding $^{13}$C-labeled 1,3-dimesitylimidazol-2-ylidene after deprotonation (Arduengo, J. A.; Dias, H. V. R.; Harlow, R. L.; Kline, M. *J. Am. Chem. Soc.*, 1992, 114 (14), pp 5530-5534). $^{13}$C enriched neopentylmagnesium chloride solution was prepared according to literature procedures starting from $^{13}$C-enriched CO$_2$ (Ahn, H.; Nicholas, C. P.; Marks, T. *J. Organometallics* 2002, 21, 1788-1806; Chabanas, M.; Baudouin, A.; Copéret, C.; Basset, J. M. *J. Am. Chem. Soc.*, 2001, 123 (9), 2062-2063). The subsequent reactions to yield the tungsten-oxo alkylidene species were carried out according to the literature (D. V. Peryshkov, R. R. Schrock, *Organometallics* 2012, 31, 7278-7286). The following compounds were all 35% $^{13}$C enriched both at the alkylidene (W=CHMe$_3$) and the NHC-carbene carbon.

Synthesis of W(O)(CHCCMe$_3$)(IMes)(Cl)$_2$ (PPhMe$_2$)

W(O)(CHCMe$_3$)(Cl)$_2$(PPhMe$_2$)$_2$ (D. V. Peryshkov, R. R. Schrock, *Organometallics* 2012, 31, 7278-7286) (300 mg, 0.486 mmol, 1 equiv.) was dissolved in 10 mL toluene and cooled to −40° C. for 1 h. A separate solution of 1,3-dimesitylimidazol-2-ylidene (148 mg, 0.486 mmol, 1 equiv.) was prepared in 2 mL of toluene and cooled to −40° C. Under stirring the cold NHC-solution was added drop wise to the cold W-complex solution. Once addition was complete, the mixture was stirred at room temperature for 30 min; then the solvent was removed in vacuo. The oily yellow orange residue was triturated with hexane until a solid was obtained. The solid was filtered off and extracted with benzene. Insoluble solids were filtered off. The benzene was removed in vacuo. The yellow orange solid was recrystallized from a mixture of diethyl ether and THF. Yield: 306 mg (80.4%). In solution the phosphine ligand is labile, which results in a second set of signals in the NMR spectrum. Only signals for the species with bound phosphine are given. $^1$H NMR (400 MHz, C$_6$D$_6$): δ=11.63 (d, $^3$J$_{P-H}$=3.4 Hz, $^1$J$_{C-H}$=124.33 Hz, 1H, W=CH), 7.49 (m, 2H, Ph-P), 6.84 (m, 3H, Ph-P), 6.82 (s, 2H, Mes-Ar), 6.81 (s, 2H, Mes-Ar), 6.20 (s, 2H, N—CH=CH—N), 2.44 (s, 6H, Mes-Me), 2.33 (s, 6H, Mes-Me), 2.10 (s, 6H, Mes-Me), 1.85 (d, J$_{P-H}$=10.57 Hz, 3H, P-Me), 1.65 (d, J$_{P-H}$=9.61 Hz, 3H, P-Me), 0.97 (s, 9H, tBu); $^{13}$C NMR (100 MHz, C$_6$D$_6$): δ=313.7 (d, J$_{C-P}$=11.27 Hz, J$_{W-C}$=153.75 Hz, W=C), 193 (d, J$_{C-P}$=71.44 Hz, J$_{W-C}$=147.1 Hz, N—C—N), 138.7 (ipso-Mes), 138.4 (d, J$_{C-P}$=38.02 Hz, P—Ar), 137.5 (p-Mes), 136 (o-Mes), 135.6 (o-Mes), 130.8 (m-Mes), 129.5 (d, J$_{C-P}$=2.07 Hz, P—Ar), 129.3 (P—Ar), 129.2 (P—Ar), 128.4 (P—Ar), 124.5 (N—CH=CH—N), 45.8 (CMe$_3$), 33.3 (C-Me$_3$), 21.1 (Mes-Me), 19.7 (Mes-Me), 19.6 (Mes-Me), 15.5 (d, J$_{C-P}$=35.31 Hz, P-Me), 13.6 (d, J$_{C-P}$=28.09 Hz, P-Me); $^{31}$P NMR (162 MHz, C$_6$D$_6$): δ=5.76 (m, bound PPhMe$_2$), −33.18 (s, free PPhMe$_2$). Anal. Calcd. for C$_{34}$H$_{45}$Cl$_2$N$_2$OPW: C, 52.12; H, 5.79; N, 3.58. Found: C, 51.81; H, 5.783; N, 3.55.

Synthesis of W(O)(CHCMe$_3$)(IMes)(OCCH$_3$(CF$_3$)$_2$) (Cl)

Inside a glove box a 25 mL Schlenk flask was charged with 285 mg (0.364 mmol) of W(O)(CHCMe$_3$)(IMes)(Cl)$_2$(PPhMe$_2$). The compound was dissolved in 5 mL of THF and cooled for 30 min at −40° C. Subsequently, 68.4 mg (0.364 mmol, 1 equiv.) of LiOCMe(CF$_3$)$_2$ were added as a solid. The suspension was left stirring at room temperature for 1 h. The solvent was removed in vacuo. An orange oily solid was obtained. It was extracted with benzene (5 mL) and separated from insoluble solids. The benzene was evaporated and the residue was recrystallized from a mixture of diethyl ether and pentane two times. A yellow crystalline solid is collected and washed with cold pentane (160 mg, 55,6%). $^1$H NMR (400 MHz, C$_6$D$_6$): δ=9.58 (s, 1H, J$_{W-H}$=7.75 Hz, J$_{C-H}$=120.9 Hz, W=CH), 6.71 (s, 2H, Mes-Ar), 6.69 (s, 2H, Mes-Ar), 6.01 (s, 2H, N—CH=CH—N), 2.17 (s, 6H, Mes-Me), 2.08 (s, 6H, Mes-Me), 2.02 (s, 6H, Mes-Me), 1.55 (s, 3H, CMe(CF$_3$)$_2$), 0.98 (s, 9H, tBu); $^{13}$C NMR (100 MHz, CD$_2$Cl$_2$): δ=284.7 (W=C), 191.8 (N—C—N), 140.6 (ipso-Mes), 137.4 (p-Mes), 136.2 (o-Mes), 135.7 (o-Mes), 130 (m-Mes), 129.8 (m-Mes), 124.6 (N—CH=CH—N), 44.3 (CMe$_3$), 31.4 (CMe$_3$), 21.3 (p-Mes-Me), 19.3 (o-Mes-Me), 19.1 (o-Mes-Me), 17.3 (OCMe(CF$_3$)$_2$), Signals for CF$_3$-groups not observed; $^{19}$F NMR (375 MHz, C$_6$D$_6$): δ=−77.07 (q, 3F, J=9.5 Hz, CF$_3$), −77.30 (q, 3F, J=9.5 Hz, CF$_3$). Anal. calcd. for C$_{30}$H$_{37}$ClF$_6$N$_2$O$_2$W: C, 45.56; H, 4.72; N, 3.54. Found: C, 45.22; H, 4.579; N, 3.44.

Synthesis of W(O)(CHCMe$_3$)(IMes)(OCCH$_3$(CF$_3$)$_2$) (OTf)

The compound was prepared by a procedure similar to that of 1 starting from W(O)(CHCMe$_3$)(IMes)(OCCH$_3$(CF$_3$)$_2$)(Cl) (131 mg, 0.166 mmol, 1 equiv.) and 1 equiv. of AgOSO$_2$CF$_3$. Yield 95 mg (63%). $^1$H NMR (400 MHz, C$_6$D$_6$): δ=10.69 (s, J$_{W-H}$=10.8 Hz, J$_{C-H}$=122.5 Hz, 1H, W=CH), 6.77 (s, 2H, Mes-Ar), 6.73 (s, 2H, N—CH=CH—N), 5.98 (s, 2H, Mes-Ar), 2.14 (s, 6H, Mes-Me), 2.12 (s, 6H, Mes-Me), 2.07 (s, 6H, Mes-Me), 1.57 (s, 3H, CMe(CF$_3$)$_2$), 0.85 (s, 9H, tBu); $^{13}$C NMR (100 MHz, C$_6$D$_6$): δ=281 (W=CH), 185.9 (N—C—N), 141.2 (ipso-Mes), 137.5 (o-Mes), 136.9 (m-Mes), 130.0 (p-Mes), 124.5 (N—CH=CH—N), 82.2 (m, CMe(CF$_3$)$_2$), 44.8 (CMe$_3$), 31.1 (CMe$_3$), 20.9 (p-Mes-Me), 18.3 (o-Mes-Me), 18.2 (o-Mes-Me), 17.7 OCMe(CF$_3$)$_2$), Signals for CF$_3$-groups not observed; $^{19}$F NMR (375 MHz, C$_6$D$_6$): δ=−77.02 (OTf), −77.21 (m, CF$_3$), −77.31 (m, CF$_3$). Anal. calcd. for C$_{31}$H$_{37}$F$_9$N$_2$O$_2$SW: C, 41.16; H, 4.12; N, 3.10. Found: C, 41.23; H, 4.157; N, 3.18.

Synthesis of [W(O)(CHCMe$_3$)(IMes)(OCCH$_3$(CF$_3$)$_2$)][B(Ar$^F$)$_4$]

W(O)(CHCMe$_3$)(IMes)(OCCH$_3$(CF$_3$)$_2$)(Cl) (78.1 mg, 0.0987 mmol) was dissolved in 5 mL of CH$_2$Cl$_2$ and cooled at −40° C. for 30 min. The solution was added to solid NaB(Ar$^F$)$_4$ (85.6 mg, 1 equiv.) The suspension was stirred for 30 min. A colorless precipitate formed. Then the solution was cooled at −40° C. for 30 min and filtered through a glass fiber filter. The filtrate was reduced in vacuo to one third of the volume and filtered again. After removing the solvent an oily foam formed. It was triturated with pentane until a bright yellow solid precipitated. The pentane phase was decanted and the solid was dried in vacuo. Yield 120 mg (75.1%). $^1$H NMR (400 MHz, CD$_2$Cl$_2$): δ=10.65 (s, $J_{W-H}$=8.9 Hz, $J_{C-H}$=121.86 Hz, 1H, W=CH), 7.72 (m, br, 8H, BAr$^F$), 7.66 (s, 2H, N—CH=CH—N), 7.56 (s, 4H, BAr$^F$), 7.17 (s, 2H, Mes-Ar), 7.14 (s, 2H, Mes-Ar), 2.39 (s, 6H, Mes-Me), 2.07 (s, 6H, Mes-Me), 2.02 (s, 6H, Mes-Me), 1.62 (s, 3H, CMe(CF$_3$)$_2$), 0.98 (s, 9H, CMe$_3$); $^{13}$C NMR (100 MHz, CD$_2$Cl$_2$): δ=301.4 (W=CH), 181.7 (N—C—N), 162.3 (q, $J_{C-B}$=49.8 Hz, 4xBC(BAr$^F$)), 143.5 (ipso-Mes), 136.1, 135.5, 135.4 (s, br, 4x2C, o-CH (BAr$^F$)), 134.5, 133.2, 131.2 (m-Mes), 131.1 (m-Mes), 129.5 (qq, $J_{C-F}$=31.6 Hz, $J_{C-B}$=2.7 Hz, 4xC—CF$_3$ (BAr$^F$)), 128.5 (N—CH=CH—N), 125.2 (q, $J_{C-F}$=272.8 Hz, 4x2CF$_3$ (BAr$^F$)), 118.1 (sept, $J_{C-F}$=3.8 Hz, p-CH (BAr$^F$)), 46.9 (CMe$_3$), 32 (CMe$_3$), 21.5 (p-Mes-Me), 19.5 (OCMe(CF$_3$)$_2$), 18.1 (o-Mes-Me), 17.9 (o-Mes-Me); $^{19}$F NMR (375 MHz, CD$_2$Cl$_2$): δ=−62.86 (BAr$^F$), −78.61 (OCMe(CF$_3$)$_2$). Anal. Calcd. for C$_{62}$H$_{49}$BF$_{30}$N$_2$O$_2$W: C, 46.01; H, 3.05; N, 1.73. Found: C, 46.09; H, 3.292; N, 1.88.

Synthesis of Mo(N-2,6-Me$_2$-C$_6$H$_3$)(CHCMe$_2$Ph)(IMes)(OC$_6$F$_5$)OTf

The reaction was carried out in a nitrogen filled glovebox. The bistriflate-NHC complex (Mo(N-2,6-Me$_2$-C$_6$H$_3$)(CHCMe$_2$Ph)(IMes)(OTf)$_2$) (388 mg, 0.41 mmol) was dissolved in 1,2-dichloroethane (15 mL) and cooled to −30° C. To this cold solution potassium pentafluorophenolate (91 mg, 0.41 mmol, 1.0 equiv.) was added as a solid. The reaction mixture was allowed to warm to room temperature and it was stirred for 3 hours. The progress of the reaction was monitored by $^1$H and $^{19}$F NMR. The precipitate was filtered out and the filtrate was evaporated under reduced pressure, the crude product was crystallized from a mixture dichloromethane/n-pentane at −30° C. yielding yellow crystalline solid as product (177 mg, 44%). $^1$H NMR (300 MHz, CD$_2$Cl$_2$): δ (ppm)=13.70 s (1H, Mo=CH), 7.30 m (5H), 7.13 s (2H, NHC—CH=CH—), 6.92 m (3H), 6.62 s (2H, Mes-H), 6.41 s (2H, Mes-H), 2.40 br (6H, Mo=N-2,6-Me$_2$-C$_6$H$_3$), 2.08 s (3H, =CHC(CH$_3$)$_2$Ph), 2.07 s (6H, Mes-CH$_3$), 2.02 s (6H, Mes-CH$_3$), 1.84 (3H, =CHC(CH$_3$)$_2$Ph), 1.76 (6H, Mes-CH$_3$). $^{19}$F NMR (282 MHz, CD$_2$Cl$_2$): δ (ppm)=−78.93 s (3F, TfO), −162.35 br (2F, o-F—C$_6$F$_5$O), −168.98 m (2F, m-F—C$_6$F$_5$O), −174.47 tt (1F, $J_{FF}$=22.1, 6.5 Hz, p-F—C$_6$F$_5$O).

Synthesis of [Mo(N-2,6-Me$_2$-C$_6$H$_3$)(CHCMe$_2$Ph)(IMes)(OC$_6$F$_5$)(MeCN)$^+$][B(Ar$^F$)$_4$]

The reaction was carried out in a nitrogen filled glovebox. The monotriflate (Mo(N-2,6-Me$_2$-C$_6$H$_3$)(CHCMe$_2$Ph)(IMes)(OC$_6$F$_5$)OTf) (168 mg, 0.17 mmol) was dissolved in dichloromethane (4 mL) and cooled to −30° C. To the cold solution of NaBAr$^F_4$ reagent (152 mg, 0.17 mmol, 1.0 equiv.) and 1.7 equiv. of MeCN (12 mg, 0.29 mmol, 15 μL) in dichloromethane (4 mL) the cold solution of molybdenum complex was added. The reaction mixture was allowed to warm to room temperature and it was stirred for additional 3 hours. The progress of the reaction was monitored by $^1$H and $^{19}$F NMR. After completion of the reaction, the precipitate was filtered out and the filtrate was evaporated to produce a yellow powder. The crude product was crystallized from a mixture of dichloromethane/n-pentane at −30° C. resulting in the pure product as yellow crystalline solid (211 mg, 71%). $^1$H NMR (300 MHz, CD$_2$Cl$_2$): δ=13.45 s (1H, Mo=CH), 7.72 br (8H, o-H—BAr$^F_4{}^-$), 7.56 br (4H, p-H-BAr$^F_4{}^-$), 7.19 m (5H), 7.07 m (3H), 6.98 m (2H), 6.84 br s (2H, Mes-H), 6.74 br s (2H, Mes-H), 2.22 s (6H, Mo=N-2,6-Me$_2$-C$_6$H$_3$), 2.22 s (6H, Mes-CH$_3$), 2.01 s (6H, Mes-CH$_3$), 1.96 s (6H, Mes-CH$_3$), 1.89 s (3H, =CHC(CH$_3$)$_2$Ph), 1.54 s (3H, =CHC(CH$_3$)$_2$Ph), 1.31 s (3H, Me CH$_3$). $^{19}$F NMR (282 MHz, CD$_2$Cl$_2$): δ (ppm)=−62.91 s (24F, CF$_3$-BAr$^F_4{}^-$), −161.20 m (2F, o-F—C$_6$F$_5$O), −165.77 m (2F, m-F—C$_6$F$_5$O), −170.75 m (1F, p-F—C$_6$F$_5$O).

Synthesis of [W(=O)(CHCMe$_2$Ph)(IMes)(OCMe(CF$_3$)$_2$)(MeCN)$^+$][B(C$_6$F$_5$)$_4$]

The reaction was carried out in a nitrogen filled glovebox. The monoalkoxide (W(=O)(CHCMe$_2$Ph)(IMes)(OCMe(CF$_3$)$_2$)(Cl)) (150 mg, 0.18 mmol) was dissolved in dichloromethane (4 mL) and cooled to −30° C. followed by the addition of the cold solution of NaB(C$_6$F$_5$)$_4$ reagent (126 mg, 0.18 mmol, 1.0 equiv.) in dichloromethane (4 mL). The reaction mixture was allowed to warm to room temperature and it was stirred for additional 3 hours. The progress of the reaction was monitored by $^1$H and $^{19}$F NMR. After completion of the reaction, the precipitate was filtered out and the filtrate was evaporated to produce a yellow powder. The crude product was crystallized from acetonitrile at −30° C. resulting in the pure product as yellow crystalline solid (206 mg, 77%). $^1$H NMR (300 MHz, CD$_2$Cl$_2$): δ (ppm)=11.61 (s, $^2J_{WH}$=6.0 Hz, 1H, W=CH), 7.37 (s, 2H, NCH IMes), 7.28 (m, 2H, Neophylidene Ph C$_{meta}$—H), 7.16 (m, 3H, Neophylidene Ph C$_{ortho}$—H, Neophylidene Ph C$_{para}$—H), 7.09 (br s, 2H, CH Mes), 2.36 (s, 6H, CH$_3$ IMes), 7.05 (br s, 2H, CH Mes), 2.12 (s, 6H, CH$_3$ IMes), 2.06 (s, 6H, CH$_3$ IMes), 1.86 (s, 3H, CH$_3$ neophylidene), 1.82 (s, 3H, CH$_3$ neophylidene), 1.55 (sept, $^4J_{HF}$=1.2 Hz, 3H, CH$_3$—OCCH(CF$_3$)$_2$). $^{19}$F NMR (282 MHz, CD$_2$Cl$_2$): δ (ppm)=−75.2 (q, $^4J_{FF}$=8.4 Hz, 3F, CF$_3$), −77.1 (q, $^4J_{FF}$=8.4 Hz, 3F, CF$_3$), −133.2 (m, 8F, C$_{orto}$—F), −163.7 (t, $^3J_{FF}$=20.3 Hz, 4F, C$_{para}$—F), −167.6 ppm (m, 8F, C$_{meta}$—F).

Synthesis of Silica-Supported [Unsaturated IMes)] Complexes According to the Invention

Synthesis of [(≡SiO)W(=O)(=CHCMe Ph)(IMes)(TfO)], 1@SiO$_2$

A yellow solution of W(O)(CHCMe$_2$Ph)(IMes)(TfO)(OCMe(CF$_3$)$_2$) (39,0 mg, 0.040 mmol, 1.05 equiv.) in benzene (5 mL) was added to a suspension of SiO$_{2-(700)}$ (0.146 g, 0.038 mmol SiOH, 1 equiv.) in benzene (2 mL) at 25° C. in an Ar filled glovebox. The suspension was slowly stirred overnight. The solid was collected by filtration and washed by suspension/filtration cycles in benzene (7*1 mL). The resulting pale yellow solid was dried thoroughly under high vacuum (10$^{-5}$ mbar) at room temperature for 4 h to afford 150 mg of the title compound. All the filtrate solutions were collected and analyzed by $^1$H NMR spectroscopy in C$_6$D$_6$ using ferrocene as internal standard indicating that 0.13 mmol of tBu$_{F_6}$OH were released upon grafting. Elemental Analysis: W 2.51%, C 5.55%, H 0.62%, N 0.40% corresponding to 34 C/W (32 expected), 45 H/W (37 expected), 3 F/W (3 expected), 2 N (2 expected).

Synthesis of [(≡SiO)W(=O)(=CHCMe$_2$Ph)(IMes)](B(Ar$^F$)$_4$), 2@SiO$_2$

A yellow solution of [W(O)(CHCMe$_2$Ph)(IMes)(OCMe(CF$_3$)$_2$)][B(Ar$^F$)$_4$] (33,4 mg, 0.019 mmol, 1.05 equiv.) was added to a suspension of SiO$_{2-(700)}$ (0.726 g, 0.018 mmol SiOH, 1 equiv.) in benzene (2 mL) at 25° C. in an Ar filled glovebox. The suspension was slowly stirred overnight. The solid was collected by filtration and washed by suspension/filtration cycles in benzene (7*1 mL). The resulting brown solid was dried thoroughly under high vacuum (10$^{-5}$ mbar) at room temperature for 4 h to afford 80 mg of the title compound. All the filtrate solutions were collected and analyzed by $^1$H NMR spectroscopy in C$_6$D$_6$ using ferrocene as internal standard indicating that 0.14 mmol of tBu$_{F_6}$OH were released upon grafting. Elemental Analysis: W 2.67%, C 11.21%, H 0.68%, F 6.22% N 0.38% corresponding to 64 C/W (63 expected), 47 H/W (49 expected), 23 F/W (24 expected), 2 N (2 expected).

Synthesis of [(≡SiO)Mo(=N-2-tBu-C$_6$H$_4$)(=CHCMe$_2$Ph)(IMes)][B(Ar$^F$)$_4$], 14@SiO2

A yellow solution of [Mo(N-2-tBu-C$_6$H$_4$)(CHCMe$_2$Ph)(IMes)-(OCH(CF$_3$)$_2$)][B(Ar$^F$)$_4$] (31,8 mg, 0.018 mmol, 1.05 equiv.) was added to a suspension of SiO$_{2-(700)}$ (0.509 g, 0.017 mmol SiOH, 1 equiv.) in benzene (2 mL) at 25° C. in an Ar filled glovebox. The suspension was slowly stirred overnight. The solid was collected by filtration and washed by suspension/filtration cycles in benzene (7*1 mL). The resulting brown solid was dried thoroughly under high vacuum (10$^{-5}$ mbar) at room temperature for 3 h to afford 80 mg of the title compound. Elemental Analysis: Mo 1.37%, C 10.84%, H 0.74%, F 7.43% N 0.71% corresponding to 62.3 C/W (73 expected), 51.4 H/W (61 expected), 27.4 F/W (24 expected), 3.5 N (3 expected).

Synthesis of [(≡SiO) Mo(N-2,6-Me$_2$-C$_6$H$_3$)(=CHCMe$_2$Ph)(IMes)][B(Ar$^F$)$_4$] 9@SiO2:

A solution of [Mo(N-2,6-Me$_2$-C$_6$H$_3$)(OC$_6$F$_5$)(IMes)(CH$_3$CN)][B(Ar$^F$)$_4$] (201 mg, 0.116 mmol, 1.05 equiv.) in a mixture of benzene (3 mL) and dichloromethane (2 mL) was added to a suspension of SiO$_{2-(700)}$ (489 mg, 0.11 mmol SiOH, 1 equiv.) in benzene (7 mL) at 25° C. in a nitrogen filled glovebox. The suspension was slowly stirred for 4 h. The solid was collected by filtration and washed by suspension/filtration cycles in benzene (5*3 mL). The resulting pale orange solid was dried thoroughly under high vacuum (10$^{-5}$ mbar) at room temperature for 4 h to afford 500 mg of the title compound. All the filtrate solutions were collected and analyzed by 1H and 19F NMR spectroscopy in C$_6$D$_6$ using dioxane as internal standard indicating that 0.22 mmol of C$_6$F$_5$OH were released upon grafting.

Synthesis of [(≡SiO)W(=O)(=CHCMe$_2$Ph)(IMes)](B(C$_6$F$_5$)$_4$), 15@SiO$_2$ A solution of [W(=O)(CHCMe$_2$Ph)(IMes)(OCMe(CF$_3$)$_2$)][B(C$_6$F$_5$)$_4$] (105 mg, 0.068 mmol, 1.05 equiv.) in a mixture of benzene (3 mL) and dichloromethane (2 mL) was added to a suspension of SiO$_{2-(700)}$ (300 mg, 0.065 mmol SiOH, 1 equiv.) in benzene (5 mL) at 25° C. in a nitrogen filled glovebox. The suspension was slowly stirred for 4 h. The solid was collected by filtration and washed by suspension/filtration cycles in benzene (5*3 mL). The resulting pale orange solid was dried thoroughly under high vacuum (10$^{-5}$ mbar) at room temperature for 4 h to afford 350 mg of the title compound. All the filtrate solutions were collected and analyzed by $^1$H and $^{19}$F NMR spectroscopy in C$_6$D$_6$ using dioxane as internal standard indicating that 0.108 mmol of tBu$_{F_6}$OH were released upon grafting.

Synthesis of [Saturated (H$_2$IMes)] Molecular Precursors for Compounds According to the Invention

Synthesis of Mo(N-2,6-Me$_2$Ph)OTf(OC$_6$F$_6$)(=CHCMe$_2$Ph)(H$_2$IMes) (M. Buchmeiser, ChemCatChem 2016, 8, 2710-2723):

The reaction was carried out in a nitrogen filled glovebox. The bistriflate (Mo(N-2,6-Me$_2$Ph)(OTf)$_2$(=CHCMe$_2$Ph)(H$_2$IMes)) (238 mg, 0.25 mmol) was dissolved in 1,2-dichloroethane (15 mL) and cooled to −30° C. To this cold solution potassium pentafluorophenolate (56 mg, 0.25 mmol, 1.0 equiv.) was added as a solid. The reaction mixture was allowed to warm to room temperature and it was stirred for 3 hours. The progress of the reaction was monitored by $^1$H and $^{19}$F NMR. The precipitate was filtered out and the filtrate was evaporated under reduced pressure, the crude was crystallized from a mixture dichloromethane/n-pentane at −30° C. yielding yellow crystalline solid as product (185 mg, 75%). $^1$H NMR (300 MHz, CD$_2$Cl$_2$): δ (ppm)=13.81 s (1H, Mo=CH), 7.36 m (2H, =CH(CH$_3$)Ph), 7.29 m (2H, =CH(CH$_3$)Ph), 7.28 m (1H, =CHC(CH$_3$)$_2$Ph), 6.80-6.95 m (3H, Mo=N-2,6-diMe-Ph), 6.56 s (2H, Mes-H), 6.36 s (2H, Mes-H), 3.78-4.08 m (4H, NHC—CH$_2$), 2.40 br (6H, Mo=N-2,6-diMe-Ph), 2.27 s (6H, Mes-CH$_3$), 2.18 s (3H, =CHC(CH$_3$)$_2$Ph), 2.01 s (6H, Mes-CH$_3$), 2.00 (6H, Mes-CH$_3$), 1.86 (3H, =CHC(CH$_3$)$_2$Ph). $^{19}$F NMR (300 MHz, CD$_2$Cl$_2$): δ (ppm)=−78.9 s (3F, TfO), −162.4 br (2F, o-F—C$_6$F$_5$O), −169.0 m (2F, m-F—C$_6$F$_5$O), −174.9 tt (1F, J$_{FF}$=22.1, 6.5 Hz, p-F—C$_6$F$_5$O).

Synthesis of [Mo(N-2,6-Me$_2$Ph)(OC$_6$F$_5$)(=CHCMe$_2$Ph)(H$_2$IMes)][B(Ar$^F$)$_4$] (M. Buchmeiser, ChemCatChem 2016, 8, 2710-2723):

The reaction was carried out in a nitrogen filled glovebox. The monotriflate (Mo(N-2,6-Me$_2$Ph)OTf(OC$_6$F$_6$)(=CHCMe$_2$Ph)(H$_2$IMes)) (177 mg, 0.18 mmol) was dissolved in dichloromathane (4 mL) and cooled to −30° C. To the cold solution of NaBAr$^F$$_4$ reagent (160 mg, 0.18 mmol, 1.0 equiv.) and 1.7 equiv. of MeCN (13 mg, 0.31 mmol, 16 µL) in dichloromethane (4 mL) the cold solution of molybdenum complex was added. The reaction mixture was allowed to warm to room temperature and it was stirred for additional 3 hours. The progress of the reaction was monitored by $^1$H and $^{19}$F NMR. After completion of the reaction, the precipitate was filtered out and the filtrate was evaporated to produce a yellow powder. The crude product was crystallized from a mixture of dichloromethane/n-pentane at −30° C. resulting in the pure product as yellow crystalline solid (251 mg, 80%). $^1$H NMR (300 MHz, CD$_2$Cl$_2$): δ=13.42 s (1H, Mo=CH), 7.72 br (8H, o-H—BAr$^F$$_4$-), 7.56 br (4H, p-H-BAr$^F$$_4$-), 7.23 m (2H, =CHC(CH$_3$)$_2$Ph), 7.16 m (1H, =CHC(CH$_3$)$_2$Ph), 7.00-7.11 m (3H, Mo=N-2,6- diMe-Ph), 6.98 m (2H, =CHC(CH$_3$)$_2$Ph), 6.77 sbr (2H, Mes-H), 6.69 br s (2H, Mes-H), 4.01 m (4H, NHC—CH$_2$), 2.26 s (6H, Mes-CH$_3$), 2.22 s (3H, =CHC(CH$_3$)$_2$Ph), 2.20 s (6H, Mes-CH$_3$), 2.17 s (6H, Mes-CH$_3$), 1.86 s (3H, =CHC(CH$_3$)$_2$Ph), 1.52 s (3H, CH$_3$), 1.32 s (3H, CH$_3$). $^{19}$F NMR (300 MHz, CD$_2$Cl$_2$): δ (ppm)=−62.9 s (24F, CF$_3$-BAr$^F_4{}^-$), −160.9 m (2F, o-F—C$_6$F$_5$O), −165.8 m (2F, m-F—C$_6$F$_5$O), −170.7 m (1F, p-F—C$_6$F$_5$O).

Synthesis of Silica-Supported [Saturated (H$_2$IMes)] Complexes According to the Invention Synthesis of [(≡SiO)Mo(2,6-Me$_2$Ph) (=CHCMe$_2$Ph)(H$_2$IMes)][B(Ar$^F$)$_4$], 10@SiO2 (M. Buchmeiser, ChemCatChem 2016, 8, 2710-2723):

A solution of [Mo(2,6-Me$_2$Ph)(=CHCMe$_2$Ph)-(OC$_6$F$_5$)(H$_2$IMes)(CH$_3$CN)][B(Ar$^F$)$_4$] (240 mg, 0.137 mmol, 1.05 equiv.) in a mixture of benzene (3 mL) and dichloromethane (5 mL) was added to a suspension of SiO$_{2-(700)}$ (580 mg, 0.13 mmol SiOH, 1 equiv.) in benzene (7 mL) at 25° C. in a nitrogen filled glovebox. The suspension was slowly stirred for 4 h. The solid was collected by filtration and washed by suspension/filtration cycles in benzene (5*3 mL). The resulting pale orange solid was dried thoroughly under high vacuum (10$^{-5}$ mbar) at room temperature for 4 h to afford 650 mg of the title compound. All the filtrate solutions were collected and analyzed by 1H and 19F NMR spectroscopy in C$_6$D$_6$ using dioxane as internal standard indicating that 0.22 mmol of C$_6$F$_5$OH were released upon grafting.

Catalytic Tests

Metathesis of cis-4-Nonene:

A t=0, a 0.95 M solution of cis-4-nonene in toluene containing heptane as internal standard (0.1 M) was added to the catalyst introduced in a conical base vial containing a wing shaped magnetic stirred, and the reaction mixture was stirred at 600 rpm and kept at 30° C. using an aluminum heating block. 5 μL aliquots of the solution were sampled, diluted with pure toluene (100 μL) and quenched by the addition of 1 μL of wet ethyl acetate. The resulting solution was analyzed by GC/FID (Agilent Technologies 7890 A) equipped with an HP-5 (Agilent Technologies) column. Conversion and EZ selectivity are shown by [eq.1,2,3]. Equilibrium conversion is reached at ca. 50%.

$$\text{Product conversion}_t = \frac{\Sigma[\text{products}]_t}{[\text{substrate}]_{ini}} \quad (1)$$

$$Z \text{ selectivity} = \frac{\Sigma[Z \text{ products}]_t}{\Sigma[\text{products}]_t} \quad (2)$$

$$E \text{ selectivity} = \frac{\Sigma[E \text{ products}]_t}{\Sigma[\text{products}]_t} \quad (3)$$

TABLE S1

Metathesis of cis-4-nonene by complexes 1@SiO$_2$, 2@SiO$_2$.

| Complex | Mol % | TOF$_{3\ min}$ (min$^{-1}$) | Time to equilibrium |
|---|---|---|---|
| 1@SiO$_2$ | 0.1 | 10 | 360 min |
| 2@SiO$_2$ | 0.1 | 90 | <5 min |
| 2@SiO$_2$ | 0.02 | 120 | 60 min |

Figure 2:
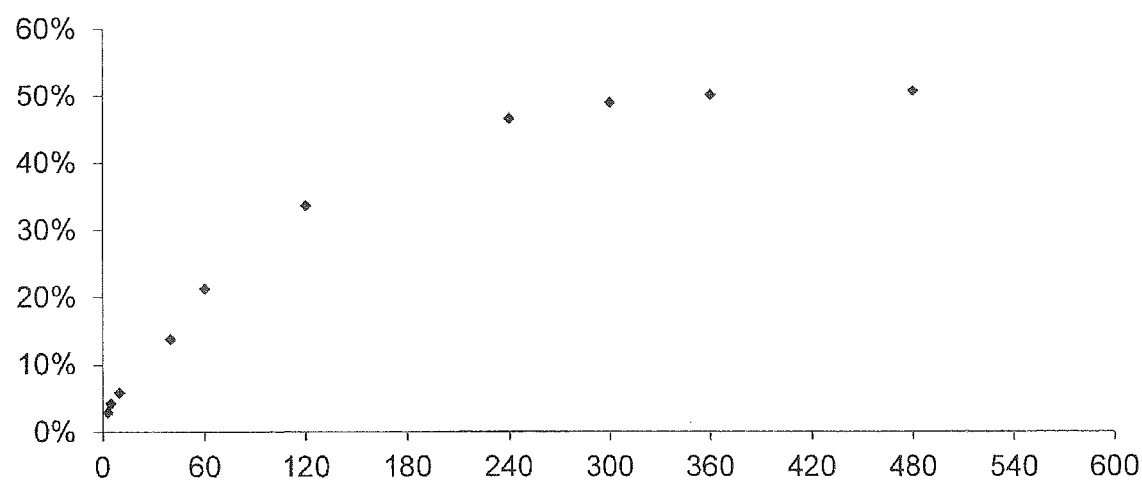
FIG. 2 shows the conversion of non-4-ene in the metathesis thereof using compound 1@SiO2 according to the invention (0.1 mol %, 30° C.). The x-axis denotes the time in minutes and the y-axis the conversion in %.

FIGS. 2 and 3 show the dependence of conversion from time, respectively the dependence of E/Z selectivity from time, when using compound 1@SiO$_2$.

FIGS. 4 and 5 show the dependence of conversion from time, respectively the dependence of E/Z selectivity from time, when using compound 2@SiO$_2$.

FIGS. 6 and 7 show the effect on conversion, respectively EZ selectivity, compared to FIG. 4, respectively FIG. 5, when the concentration of compound 2@SiO$_2$ is reduced from 0.1 mol % to 0.02 mol %.

Metathesis of 1-nonene:

A t=0, a 0.79 M solution of 1-nonene in toluene containing heptane as internal standard (0.08 M) was added to the catalyst introduced in a conical base vial containing a wing shaped magnetic stirrer, and the reaction mixture was stirred at 600 rpm and kept at 30° C. using an aluminum heating block. 5 μL aliquots of the solution were sampled (by opening the vial), diluted with pure toluene (100 μL) and quenched by the addition of 1 μL of wet ethyl acetate. The resulting solution was analyzed by GC/FID (Agilent Technologies 7890 A) equipped with an HP-5 (Agilent Technologies) column. Equilibrium conversion is reached at ca. 93% in our conditions.

TABLE S2

Metathesis of 1-nonene by complexes 1@SiO$_2$, 2@SiO$_2$ (0.02 mol %, 30° C.).

| Complex | TOF$_{3\ min}$ (min$^{-1}$) | Time to equilibrium |
|---|---|---|
| 1@SiO$_2$ | 4 | 26% of conversion after 24 h |
| 2@SiO$_2$ | 421 | 17 h (92% of conversion) |

TABLE S3

Metathesis of 1-nonene by complexes 2@SiO$_2$ (0.002 mol %, 30° C.).

| Complex | TOF$_{3\ min}$ (min$^{-1}$) | Time to equilibrium |
|---|---|---|
| 2@SiO$_2$ | 2457 | 74% of conversion after 24 h |

TABLE S4

Metathesis of 1-nonene by complexes 2@SiO$_2$ (0.0001 mol %, 30° C.).

| Complex | TOF$_{3\ min}$ (min$^{-1}$) | Time to equilibrium |
|---|---|---|
| 2@SiO$_2$ | 831 | 61% of conversion after 24 h |

TABLE S5

Metathesis of 1-nonene by complexes 2@SiO$_2$ (0.0001 mol %, 70° C.)

| Complex | TOF$_{3\ min}$ (min$^{-1}$) | Time to equilibrium |
|---|---|---|
| 2@SiO$_2$ | 1046 | 58% of conversion after 24 h |

Metathesis of Ethyl Oleate:

A t=0, a 0.53 M solution of ethyl oleate in toluene containing octadecane as internal standard (0.08 M) was added to the catalyst introduced in a conical base vial containing a wing shaped magnetic stirred, and the reaction mixture was stirred at 600 rpm and kept at 30° C. using an aluminum heating block. 5 μL aliquots of the solution were sampled (by opening the vial), diluted with pure toluene (100 μL) and quenched by the addition of 1 μL of wet ethyl acetate. The resulting solution was analyzed by GC/FID (Agilent Technologies 7890 A) equipped with an HP-88 (Agilent Technologies) column. Conversion and E/Z selectivity are shown by [eq.1,2,3]. Equilibrium conversion is reached at ca. 50%.

TABLE S6

Metathesis of ethyl oleate by compound 2@ SiO$_2$ (0.1 mol %, 30° C.).

| Complex | TOF$_{3\,min}$ (min$^{-1}$) | Time to equilibrium |
|---|---|---|
| 2@SiO$_2$ | <1 | 8 h |

TABLE S7

Metathesis of ethyl oleate by compound 2@ SiO$_2$ (0.001 mol %, 70° C.).

| Complex | TOF$_{3\,min}$ (min$^{-1}$) | Time to equilibrium |
|---|---|---|
| 2@SiO$_2$ | 400 | 13% after 1 h |

Metathesis of Diallyl Ether

A t=0, a 0.1 M solution of diallyl ether in toluene was added to the catalyst introduced in a Schlenk flask and the reaction mixture was stirred at 500 rpm and kept at 30° C. using an aluminum heating block. 0.5 mL aliquots of the solution were sampled, diluted with deuterated benzene (1 mL) and analyzed by NMR.

Metathesis of Diallyldiphenylsilane

A t=0, a 0.1 M solution of diallyldiphenylsilane in toluene was added to the catalyst introduced in a Schlenk flask and the reaction mixture was stirred at 500 rpm and kept at 30° C. using an aluminum heating block. 0.5 mL aliquots of the solution were sampled, diluted with deuterated benzene (1 mL) and analyzed by NMR.

Ethenolysis of Ethyl Oleate

Ethyl oleate (1.51 mmol, 470.2 mg) was weighed into a liner inside a glovebox and a suspension of the 2@SiO$_2$ (10.5 mg, 1.52 µmol, 0.1 mol %) in 1 ml toluene added. The glass liner was then placed in a heated reactor block, the autoclave sealed, pressurized to 10 bar ethylene (3 fill-release cycles) and heated to 60° C. for 1 hour under constant ethylene pressure (10 bar) and 600 rpm mechanical stirring. After this time, the reactor was cooled down under ethylene and opened. Quantification of the liquid phase by GC indicated a final conversion of 93% with 82% selectivity for the cross metathesis products (1-decene and ethyl 9-decenoate).

Propene Metathesis Test in Flow Reactor

The selected catalyst (15 mg, 2.18 mmol) mixed with 2.5 g SiC was loaded into the flow reactor in the glove box. The reactor was then connected to the PID Microactivity instrument, and the connections were flushed with argon:propene 2:1 mixture (in volume) for 2 h. The flow rate of the argon:propene 2:1 mixture was then set to 60 mL.min$^{-1}$, 1.5 Bar (565 mol propene/mol W/min$^{-1}$) and the temperature set to 30° C. The opening of the valve connecting the reactor to the gas line corresponds to the beginning of the catalytic test. The reaction was monitored by GC using an auto-sampler.

Catalyst Recycling, Cis-4-Nonene Test

Stepa: A 0.96 M solution of cis-4-nonene in toluene containing heptane as internal standard (0.1 M) was added to 2@SiO2 (catalyst to substrate ratio 1000) in a conical base vial containing a wing shaped magnetic stirrer. Stepb: The reaction mixture was stirred at 600 rpm and kept at 30° C. using an aluminum heating block for 30 min, sampling reaction mixture after 3, 5, 10 and 30 minutes. After leaving the supported catalyst settling, the olefin mixture was filtered out, the catalyst was washed with toluene and replaced by the same amount of fresh cis-non-4-ene solution, keeping the catalyst to substrate ratio to 1000. Step b was repeated three times and without any noticeable loss of activity of the catalyst (see Table S8).

TABLE S8

TON (TON is the turnover number and symbolizes the number of chemical conversions of the substrate molecules per time unit with regard to the used catalyst) (min$^{-1}$) at 3 min and % of productive conversion (equilibrium conversion correspond to ca 50%) after 30 min during the cycles described above for 2@SiO2

| Cycle | TON (min$^{-1}$) | % of conversion |
|---|---|---|
| I | 86 | 50 |
| Ii | 88 | 50 |
| Iii | 90 | 50 |

Catalyst Recycling, 1-Nonene Test

Stepa: A 0.8 M solution of 1-nonene in toluene containing heptane as internal standard (0.1 M) was added to 2@SiO2 (catalyst to substrate ratio 1000) in a conical base vial containing a wing shaped magnetic stirrer. Stepb: The reaction mixture was stirred at 600 rpm and kept at 30° C. using an aluminum heating block for 30 min, sampling reaction mixture after 3 and 5 minutes. After leaving the supported catalyst settling, the olefin mixture was filtered out, the catalyst was washed with toluene and replaced by the same amount of fresh 1-nonene solution, keeping the catalyst to substrate ratio to 1000. Step b was repeated three times (Table S9).

TABLE S9

TON (min$^{-1}$) at 3 min and % of productive conversion (equilibrium conversion correspond to ca 50%) after 5 min during the cycles described above for 2@SiO2

| Cycle | TON (min$^{-1}$) | % of conversion |
|---|---|---|
| I | 167 | 61 |
| Ii | 123 | 51 |
| Iii | 129 | 52 |

FIG. 8 shows the dependence of conversion from time of propene by compound 2@SiO$_2$ according to the invention under flow conditions in a flow reactor, and FIG. 9 shows TONs (y-axis) of propene metathesis by compound 2@SiO$_2$ under flow conditions (x-axis: time in days).

Comparison of Catalyst Efficacy in Homometathesis of Methyl-9-Dodecenoate (DDAME)

[(≡SiO)Mo(NAr)(=CHCMe$_2$Ph)(Me$_2$Pyr)] (Ar=2,6-di-isopropyl-phenyl; Me2Pyr=2,5-dimethylpyrrolide) was prepared according to WO 2015/003815 for comparison. The efficacy of compound 2@SiO$_2$ was compared to in homometathesis of methyl-9-dodecenoate (DDAME) by 100 ppm mol (0.01 mol %) catalysts, at 120° C. after 1 h and 5 h. The results are summarized in Table S10:

TABLE S10

| | Comparison | 2@SiO$_2$ |
|---|---|---|
| Conversion [%] after 1 h | 37 | 51 |
| Conversion [%] after 5 h | 38 | 51 |

Method of Converting a Compound According to the Invention into Another Compound According to the Invention by Alkylidene Exchange Synthesis of [(≡SiO)W(=O)(=CH(2-CH$_3$O)Ph)(IMes)][B(Ar$^F$)$_4$], 11@SiO$_2$:

A solution of 2-methoxystyrene (2.7 mg, 0.020 mmol, 2.0 equiv.) in benzene (1 mL) was added to a suspension of [(≡SiO)W(=O)(=CHCMe$_2$Ph)(IMes)][B(Ar$^F$)$_4$], 2@SiO$_2$, (100 mg, 0.099 mmol) in benzene (2 mL) at 25° C. in a nitrogen filled glovebox and the suspension was slowly stirred for 2 h. The solid was collected by filtration and washed by suspension/filtration cycles in benzene (3*3 mL). The resulting dark red solid was dried under high vacuum (10$^{-5}$ mbar) at room temperature for 2 h to afford 90 mg of the title compound. All the filtrate solutions were collected and analyzed by 1H NMR spectroscopy in C$_6$D$_6$ using ferrocene as internal standard indicating that 0.09 mmol of =CHCMe$_2$Ph were released upon alkylidene exchange reaction.

Synthesis of [(≡SiO)Mo(N-2,6-Me$_2$Ph)(=CH(2-CH$_3$O)Ph)(IMes)][B(Ar$^F$)$_4$], 13@SiO$_2$:

A solution of 2-methoxystyrene (5.9 mg, 0.044 mmol, 2.0 equiv.) in benzene (1 mL) was added to a suspension of [(≡SiO)Mo(N-2,6-Me$_2$Ph)(=CHCMe$_2$Ph)(IMes)][B(Ar$^F$)$_4$], 9@SiO$_2$ in the form of its complex with acetonitrile, (100 mg, 0.022 mmol) in benzene (2 mL) at 25° C. in a nitrogen filled glovebox and the suspension was slowly stirred for 2 h. The solid was collected by filtration and washed by suspension/filtration cycles in benzene (3*3 mL). The resulting dark red solid was dried under high vacuum (10$^{-5}$ mbar) at room temperature for 2 h to afford 95 mg of the title compound. All the filtrate solutions were collected and analyzed by 1H NMR spectroscopy in C$_6$D$_6$ using ferrocene as internal standard indicating that 0.21 mmol of =CHCMe$_2$Ph were released upon alkylidene exchange reaction.

Synthesis of [(≡SiO)Mo(N-2,6-Me$_2$Ph)(=CH(2-CH$_3$O)Ph)(H$_2$IMes)][B(Ar$^F$)$_4$], 12@SiO$_2$:

A solution of 2-methoxystyrene (5.9 mg, 0.044 mmol, 2.0 equiv.) in benzene (1 mL) was added to a suspension of [(≡SiO)Mo(N-2,6-Me$_2$Ph)(=CHCMe$_2$Ph)(H$_2$IMes)][B(Ar$^F$)$_4$], 10@SiO$_2$ in the form of its complex with acetonitrile, (100 mg, 0.022 mmol) in benzene (2 mL) at 25° C. in a nitrogen filled glovebox and the suspension was slowly stirred for 2 h. The solid was collected by filtration and washed by suspension/filtration cycles in benzene (3*3 mL). The resulting dark red solid was dried under high vacuum (10$^{-5}$ mbar) at room temperature for 2 h to afford 95 mg of the title compound. All the filtrate solutions were collected and analyzed by 1H NMR spectroscopy in C$_6$D$_6$ using ferrocene as internal standard indicating that 0.21 mmol of =CHCMe$_2$Ph were released upon alkylidene exchange reaction.

The invention claimed is:

1. A compound of general Formula I or Formula II

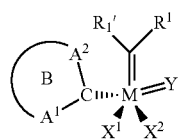

I

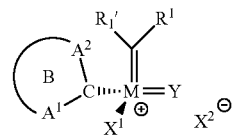

II wherein:
A$^1$ is NR$^2$ or PR$^2$;
A$^2$ is CR$^2$R$^{2'}$, NR$^2$, PR$^2$, O or S;
C is a carbene carbon atom;
ring B includes A$^1$—C—A$^2$ and is a unsubstituted or mono- or multisubstituted 5 to 7-membered ring, which may contain besides A$^1$ and A$^2$ further heteroatoms selected from nitrogen, phosphorus, oxygen or sulfur, and the substituents of which have the meaning of R$^2$;
R$^2$ and R$^{2'}$ are independently from one another H, a linear, a partially cyclic or branched C$_1$ to C$_{18}$-alkyl residue, a linear, a partially cyclic or branched C$_1$ to C$_{18}$-alkenyl residue, a C$_3$ to C$_{12}$-cycloalkyl residue, a linear, partially cyclic or branched C$_6$ to C$_{100}$-polyoxaalkyl residue, a C$_5$ to C$_{14}$-aryl or heteroaryl residue, a C$_3$ to C$_{14}$-aryloxy residue, a linear, partially cyclic or branched C$_1$ to C$_{18}$-perfluoroalkyl residue, a linear, partially cyclic or branched C$_1$ to C$_{18}$-perchloroalkyl residue, a linear, partially cyclic or branched partially fluorinated C$_1$ to C$_{18}$-alkyl residue, a partially chlorinated linear, partially cyclic or branched C$_1$ to C$_{18}$-alkyl residue, a perfluorinated or partially fluorinated C$_6$ to C$_{14}$-aryl residue, a perchlorinated or partially chlorinated C$_6$ to C$_{14}$-aryl residue;
and, when A$^1$ and A$^2$ are NR$^2$ or PR$^2$, respectively, R$^2$ may be the same or may be different, or
R$^2$ and R$^{2'}$ taken together form a linear or branched C$_1$ to C$_{18}$-alkylene residue;
M is Cr, Mo or W;
X$^1$ is a residue of a solid oxide, wherein the solid oxide is linked to M via oxygen;
X$^2$ is selected from the group comprising or consisting of halogenide, C$_1$ to C$_{18}$-carboxylates, C$_1$ to C$_{18}$-alkoxides, fluorinated C$_1$ to C$_{18}$-alkoxides, C$_1$ to C$_{18}$-mono- or polyhalogenated carboxylates, unsubstituted, mono or multisubstituted C$_6$ to C$_{18}$-monophenolate, -biphenolate or -terphenolate, wherein the substituents at the monophenolate, bisphenolate or terphenolate have the meaning of halogen or R$^2$, C$_1$ to C$_{18}$-thiolate, unsubstituted, mono or multisubstituted C$_6$ to C$_{18}$-monothiophenolate, -thiobiphenolate or -thioterphenolate, wherein the substituents at the thiomonophenolate, thiobisphenolate or thioterphenolate have the meaning of halogen or R$^2$, trifluoromethane sulfonate, pyrrol-1-yl, optionally substituted with one or more of R$^2$, —NH—(CO)—R$^2$, —N(R$^2$)$_2$, wherein R$^2$ is selected independently from one another, or non-coordinating anions;
Y is oxygen, sulfur, N-adamantyl, N-tert-butyl, N—(C$_{6-14}$)aryl, wherein aryl may be substituted with one or more of halogen, linear or branched C$_1$ to C$_{18}$-alkyl, linear or branched C$_1$ to C$_{18}$-alkyloxy or substituted or unsubstituted phenyl, the substituents of which have the meaning of R$^2$;
R$^1$ and R$_1$' are independently from one another H, linear or branched C$_1$ to C$_{18}$-alkyl or unsubstituted or substituted C$_6$ to C$_{14}$-aryl, wherein the substituents have the meaning of R$^2$; or R1 and R$_1$' are independently from one another ortho-alkoxyphenyl, wherein alkoxy is $C_1$ to $C_6$-alkoxy; or wherein $R_1$ and $R_1'$ are independently from one another H and ortho-alkoxyphenyl, wherein alkoxy is $C_1$ to $C_6$-alkoxy.

2. The compound according to claim 1, wherein M is Mo or W.

3. The compound according to claim 1, wherein Y is oxygen.

4. The compound according to claim 1, wherein $R^1$ and $R_1'$ are independently from one another H and tert-butyl, or H and $CMe_2Ph$; or wherein at least one of $R^1$ and $R_1'$ is ortho-alkoxyphenyl, wherein alkoxy is $C_1$ to $C_6$-alkoxy; or wherein $R^1$ and $R_1'$ are independently from one another H and ortho-alkoxyphenyl, wherein alkoxy is $C_1$ to $C_6$-alkoxy.

5. The compound according to claim 1, wherein ring B is a heterocycle selected from the group comprising or consisting of: 1,3-disubstituted imidazol-2-ylidene, 1,3-disubstituted imidazolidin-2-ylidene, 1,3-disubstituted tetrahydropyrimidin-2-ylidene, 1,3-disubstituted diazepin-2-ylidene, 1,3-disubstituted dihydro-diazepin-2-ylidene, 1,3-disubstituted tetrahydrodiazepin-2-ylidene, N-substituted thiazol-2-ylidene, N-substituted thiazolin-2-ylidene, N-substituted triazol-2-ylidene, N-substituted dihydrotriazol-2-ylidene, mono- or multisubstituted triazolin-2-ylidene, N-substituted thiadiazol-2-ylidene, mono- or multisubstituted thiadiazolin-2-ylidene and mono- or multi-substituted tetrahydrotriazol-2-ylidene, wherein the heterocycle may have one or more further substituents, wherein said substituents independently have the meaning of $R^2$ or halogen or $NR^2$.

6. The compound according to claim 5, wherein ring B is selected from 1,3-dimesitylimidazol-2-ylidene, 1,3-dimesitylimidazolidin-2-ylidene, 1,3-di-tert-butylimidazol-2-ylidene, 1,3-di-tent-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene.

7. The compound according to claim 1, wherein when $X^2$ is a non-coordinating anion, said anion in Formula II is selected from tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

8. The compound according to claim 1, wherein the solid oxide is selected from the group comprising or consisting of: silica, titania, zirconia, cerium oxide, alumina, or a mixture of two or more thereof.

9. The compound according to claim 1, wherein the solid oxide is silica and $X^1$ is O—Si(O—)$_3$.

10. The compound according to claim 9, wherein silica is comprised in a solid support.

11. The compound according to claim 1, wherein
M is selected from Mo or W;
Y is selected from oxygen, sulfur, N-adamantyl, N-tert-butyl, N—($C_{6-14}$)aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;
ring B is selected from 1,3-dimesitylimidazol-2-ylidene, 1,3-dimesitylimidazolidin-2-ylidene, 1,3-di-tert-butyl-imidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene;
$R^1$ and $R_1'$ are independently from one another H and tert-butyl, or H and $CMe_2Ph$; or wherein at least one of $R^1$ and $R_1'$ is ortho-alkoxyphenyl, wherein alkoxy is $C_1$ to $C_6$-alkoxy; or wherein $R^1$ and $R_1'$ are independently from one another H and ortho-alkoxyphenyl, wherein alkoxy is $C_1$ to $C_6$-alkoxy;
$X^1$ is (—O—)$_3$Si—O—; and
$X^2$ is selected from the group comprising or consisting of halide, $C_1$ to $C_{18}$-alkoxides, fluorinated $C_1$ to $C_{18}$-alkoxides, trifluoromethane sulfonate, tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate; or
wherein
M is selected from Mo or W;
Y is selected from oxygen, N-adamantyl, N-tert-butyl, N—($C_{6-14}$)aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;
ring B is selected from 1,3-dimesitylimidazol-2-ylidene, 1,3-dimesitylimidazolidin-2-ylidene, 1,3-di-tert-butyl-imidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene;
$R^1$ and $R_1'$ are independently from one another H and tert-butyl, or H and $CMe_2Ph$; or wherein at least one of $R^1$ and $R_1'$ is ortho-alkoxyphenyl, wherein alkoxy is $C_1$ to $C_6$-alkoxy; or wherein $R^1$ and $R_1'$ are independently from one another H and ortho-alkoxyphenyl, wherein alkoxy is $C_1$ to $C_6$-alkoxy;
$X^1$ is (—O—)$_3$Si—O—; and
$X^2$ is selected from the group comprising or consisting of F and Cl, fluorinated $C_1$ to $C_{18}$-alkoxides, trifluoromethane sulfonate, tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate; or
wherein
M is selected from Mo or W;
Y is selected from oxygen, N-adamantyl, N-tert-butyl, N—($C_{6-14}$)aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;

ring B is selected from 1,3-dimesitylimidazol-2-ylidene, 1,3-dimesitylimidazolidin-2-ylidene, 1,3-di-tert-butyl-imidazol-2-ylidene, 1,3-di-tert-butylimidazolidin-2-ylidene, 1,3-diisopropylimidazol-2-ylidene, 1,3-diisopropylimidazolidin-2-ylidene 1,3-dimethyl-benzimidazol-2-ylidene, 1,3-dicyclohexylimidazol-2-ylidene, 1,3-dicyclohexylimidazolidin-2-ylidene, 1-mesityl-3-[2-(pyridine-2-yl)-2-eth-2-yl]imidazole-2-ylidene, 1-mesityl-3-(2-phenyl-eth-2-yl)-imidazol-2-ylidene, 1-mesityl-3-(2-phenyl-eth-2-yl)-imidazolidin-2-ylidene, 4,5-dichloro-1,3-dimethyl-2-imidazol-2-ylidene, 1,3,5-triphenyl-triazol-2-ylidene, 3,5-tetramethyl-1-mesityl-pyrrolidin-2-ylidene;

$R^1$ and $R_1'$ are independently from one another H and tert-butyl, or H and $CMe_2Ph$; or wherein at least one of $R^1$ and $R_1'$ is ortho-alkoxyphenyl, wherein alkoxy is $C_1$ to $C_6$-alkoxy; or wherein $R^1$ and $R_1'$ are independently from one another H and ortho-alkoxyphenyl, wherein alkoxy is $C_1$ to $C_6$-alkoxy;

$X^1$ is $(-O-)_3Si-O-$; and $X^2$ is selected from the group comprising or consisting of F and Cl, trifluoromethane sulfonate, tetrakis(3,5-bis(trifluoromethyl)phenyl)borate, tetrakis(pentafluorophenyl)borate, tetrakis(nonafluoro-t-butoxy)aluminate, tetrafluoroborate, hexafluorophosphate and hexafluoroantimonate.

12. The compound according to claim 1, wherein
M is W;
Y is oxygen;
ring B is 1,3-dimesitylimidazol-2-ylidene;
$R^1$ and $R_1'$ are independently from one another H and $CMe_2Ph$;
$X^1$ is $(-O-)_3Si-O-$; and
$X^2$ is trifluoromethane sulfonate;
or
M is W;
Y is oxygen;
ring B is 1,3-dimesitylimidazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is W;
Y is N-tert-butyl;
ring B is 4,5-dichloro-1,3-dimethyl-imidazol-2-ylidene;
$R^1$ and $R_1'$ are independently from one another H and tert-butyl;
$X^1$ is $(-O-)_3Si-O-$; and
$X^2$ is Cl;
or
M is W;
Y is N-tert-butyl;
ring B is 4,5-dichloro-1,3-dimethyl-imidazol-2-ylidene;
$R^1$ and $R_1'$ are independently from one another H and tert-butyl;
$X^1$ is $(-O-)_3Si-O-$; and
$X^2$ is tetrakis(nonafluoro-t-butoxy)aluminate;
or
M is W;
Y is O;
ring B is 1,3,5-triphenyl-triazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is N-2,6-dichlorophenyl;
ring B is 1,3,5-triphenyl-triazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is N-2-trifluoromethylphenyl;
ring B is 1,3,5-triphenyl-triazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is N-3,5-dimethylphenyl;
ring B is 1,3,5-triphenyl-triazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is N-2,6-dimethylphenyl;
ring B is 1,3-dimesitylimidazol-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is Mo;
Y is N-2,6-dimethylphenyl;
ring B is 1,3-dimesitylimidazolidin-2-ylidene;
$R^1$ and $R_1'$ are independently from one another H and $CMe_2Ph$;
$X^1$ is $(-O-)_3Si-O-$; and
$X^2$ is tetrakis(3,5-bis(trifluoromethyl)phenyl)borate;
or
M is W;
Y is O;
ring B is 1,3-dimesitylimidazol-2-ylidene;
$R^1$ and $R_1'$ are independently from one another H and 2-methoxyphenyl;
$X^1$ is $(-O-)_3Si-O-$; and
$X^2$ is tetrakis(3,5-bis(trifluoromethyl)phenyl)borate;
or
M is Mo;
Y is N-2,6-dimethylphenyl;
ring B is 1,3-dimesitylimidazolidin-2-ylidene;
$R^1$ and $R_1'$ are independently from one another H and 2-methoxyphenyl;
$X^1$ is $(-O-)_3Si-O-$; and
$X^2$ is tetrakis(3,5-bis(trifluoromethyl)phenyl)borate;
or
M is Mo;
Y is N-2,6-dimethylphenyl;
ring B is 1,3-dimesitylimidazol-2-ylidene;
$R^1$ and $R_1'$ are independently from one another H and 2-methoxyphenyl;
$X^1$ is $(-O-)_3Si-O-$; and
$X^2$ is tetrakis(3,5-bis(trifluoromethyl)phenyl)borate;
or
M is Mo;
Y is N-2-tert-butylphenyl;
ring B is 1,3-dimesitylimidazol-2-ylidene;

$R^1$ and $R_1{'}$ are independently from one another H and $CMe_2Ph$;
$X^1$ is $(-O-)_3Si-O-$; and
$X^2$ is tetrakis(3,5-bis(trifluoromethyl)phenyl)borate;
or
M is W;
Y is O;
ring B is 1,3-dimesitylimidazol-2-ylidene;
$R^1$ and $R_1{'}$ are independently from one another H and $CMe_2Ph$;
$X^1$ is $(-O-)_3Si-O-$; and
$X^2$ is tetrakis(pentafluorophenyl)borate.

13. A method of making a compound of the general Formula I or II as defined in claim 1, comprising at least the following step (S):
   (S): reacting a solid oxide with a compound of the general Formula III or IV

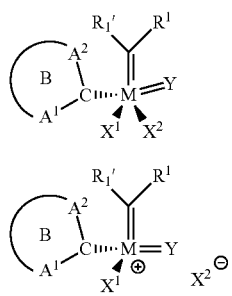

wherein:
$A^1$ is $NR^2$ or $PR^2$;
$A^2$ is $CR^2R^{2'}$, $NR^2$, $PR^2$, O or S;
C is a carbene carbon atom;
ring B includes $A^1-C-A^2$ and is a unsubstituted or mono- or multisubstituted 5 to 7-membered ring, which may contain besides $A^1$ and $A^2$ further heteroatoms selected from nitrogen, phosphorus, oxygen or sulfur, and the substituents of which have the meaning of $R^2$;
$R^2$ and $R^{2'}$ are independently from one another H, a linear, a partially cyclic or branched $C_1$ to $C_{18}$-alkyl residue, a linear, a partially cyclic or branched $C_1$ to $C_{18}$-alkenyl residue, a $C_3$ to $C_{12}$-cycloalkyl residue, a linear, partially cyclic or branched $C_6$ to $C_{100}$-polyoxaalkyl residue, a $C_5$ to $C_{14}$-aryl or heteroaryl residue, a $C_3$ to $C_{14}$-aryloxy residue, a linear, partially cyclic or branched $C_1$ to $C_{18}$-perfluoroalkyl residue, a linear, partially cyclic or branched $C_1$ to $C_{18}$-perchloroalkyl residue, a linear, partially cyclic or branched partially fluorinated $C_1$ to $C_{18}$-alkyl residue, a partially chlorinated linear, partially cyclic or branched $C_1$ to $C_{18}$-alkyl residue, a perfluorinated or partially fluorinated $C_6$ to $C_{14}$-aryl residue, a perchlorinated or partially chlorinated $C_6$ to $C_{14}$-aryl residue;
and, when $A^1$ and $A^2$ are $NR^2$ or $PR^2$, respectively, $R^2$ may be the same or may be different, or
$R^2$ and $R^{2'}$ taken together form a linear or branched $C_1$ to $C_{18}$-alkylene residue;
M is Cr, Mo or W;
$X^2$ is selected from the group comprising or consisting of halogenide, $C_1$ to $C_{18}$-carboxylates, $C_1$ to $C_{18}$-alkoxides, fluorinated $C_1$ to $C_{18}$-alkoxides, $C_1$ to $C_{18}$-mono- or polyhalogenated carboxylates, unsubstituted, mono or multisubstituted $C_6$ to $C_{18}$-monophenolate, -biphenolate or -terphenolate, wherein the substituents at the monophenolate, bisphenolate or terphenolate have the meaning of halogen or $R^2$, $C_1$ to $C_{18}$-thiolate, unsubstituted, mono or multisubstituted $C_6$ to $C_{18}$-monothiophenolate, -thiobiphenolate or -thioterphenolate, wherein the substituents at the thiomonophenolate, thiobisphenolate or thioterphenolate have the meaning of halogen or $R^2$, trifluoromethane sulfonate, pyrrol-1-yl, optionally substituted with one or more of $R^2$, $-NH-(CO)-R^2$, $-N(R^2)_2$, wherein $R^2$ is selected independently from one another, or non-coordinating anions;
Y is oxygen, sulfur, N-adamantyl, N-tert-butyl, $N-(C_{6-14})$aryl, wherein aryl may be substituted with one or more of halogen, linear or branched $C_1$ to $C_{18}$-alkyl, linear or branched $C_1$ to $C_{18}$-alkyloxy or substituted or unsubstituted phenyl, the substituents of which have the meaning of $R^2$;
$R^1$ and $R_1{'}$ are independently from one another H, linear or branched $C_1$ to $C_{18}$-alkyl or unsubstitued or substituted $C_6$ to $C_{14}$-aryl, wherein the substituents have the meaning of $R^2$; or $R1$ and $R_1{'}$ are independently from one another ortho-alkoxyphenyl, wherein alkoxy is $C_1$ to $C_6$-alkoxy; or wherein $R_1$ and $R_1{'}$ are independently from one another H and ortho-alkoxyphenyl, wherein alkoxy is $C_1$ to $C_6$-alkoxy; and
$X^1$ is $C_{0-8}$ sulfonate; halogenide; nitrate and phosphate and $C_{1-8}$ esters of phosphate; $C_{1-8}$ alcoholate.

14. The method according to claim 13, further comprising step (R) prior to step (S):
   (R): heating the solid oxide.

15. A method of forming an olefin from a first and a second olefin in a metathesis reaction, comprising step (T):
   (T): reacting the first olefin with the second olefin in the presence of a compound of general Formula I or II as defined in claim 1;
   wherein the first and the second olefin may be the same or may be different from one another.

16. A method of converting a compound of general Formula I or general Formula II as defined in claim 1 into a compound of general Formula VI or general Formula VII, comprising at least step (U):
   (U): reacting said compound of general Formula I with a compound of general Formula V to yield said compound of general Formula VI, or reacting said compound of general Formula II with a compound of general Formula V to yield said compound of general Formula VII,

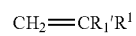

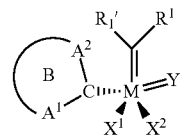

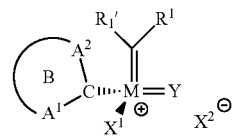

wherein at least one of $R_1{'}$ and $R^1$ in compound of Formula V is different from at least one of $R_1{'}$ and $R^1$ as defined in general Formula I or general Formula II, and wherein $R_1{'}$ and $R^1$ in general Formula VI and general Formula VII have the same meaning as in general Formula V.

* * * * *